(12) United States Patent
Kang et al.

(10) Patent No.: US 11,967,076 B2
(45) Date of Patent: Apr. 23, 2024

(54) METHOD AND DEVICE FOR PROCESSING PATHOLOGICAL SLIDE IMAGE

(71) Applicant: LUNIT INC., Seoul (KR)

(72) Inventors: Jeong Seok Kang, Yongin-si (KR); Dong Geun Yoo, Seoul (KR); Soo Ick Cho, Seoul (KR); Won Kyung Jung, Seoul (KR)

(73) Assignee: LUNIT INC., Seoul (KR)

( * ) Notice: Subject to any disclaimer, the term of this patent is extended or adjusted under 35 U.S.C. 154(b) by 0 days.

(21) Appl. No.: 18/122,837

(22) Filed: Mar. 17, 2023

(65) Prior Publication Data

US 2023/0298171 A1 Sep. 21, 2023

(30) Foreign Application Priority Data

Mar. 18, 2022 (KR) .................. 10-2022-0033928
Nov. 21, 2022 (KR) .................. 10-2022-0156241

(51) Int. Cl.
| | |
|---|---|
| *G06K 9/00* | (2022.01) |
| *G06F 3/14* | (2006.01) |
| *G06T 7/00* | (2017.01) |
| *G06V 10/74* | (2022.01) |
| *G16H 15/00* | (2018.01) |
| *G16H 50/20* | (2018.01) |

(52) U.S. Cl.
CPC .............. *G06T 7/0012* (2013.01); *G06F 3/14* (2013.01); *G06V 10/761* (2022.01); *G16H 15/00* (2018.01); *G16H 50/20* (2018.01); *G06T 2207/20081* (2013.01); *G06T 2207/30024* (2013.01)

(58) Field of Classification Search
None
See application file for complete search history.

(56) References Cited

U.S. PATENT DOCUMENTS

| | | | |
|---|---|---|---|
| 2020/0387635 A1 | 12/2020 | Lo et al. | |
| 2021/0398278 A1* | 12/2021 | Locke | ............. G06T 7/194 |
| 2022/0237788 A1* | 7/2022 | Shaul | ............. G06V 20/698 |

FOREIGN PATENT DOCUMENTS

| | | |
|---|---|---|
| WO | 2019/110583 A1 | 6/2019 |
| WO | 2022/035609 A1 | 2/2022 |

OTHER PUBLICATIONS

Extended European Search Report dated Aug. 11, 2023 in Application No. 23161701.0.

* cited by examiner

*Primary Examiner* — Wei Wen Yang
(74) *Attorney, Agent, or Firm* — Sughrue Mion, PLLC

(57) ABSTRACT

A computing device includes at least one memory, and at least one processor configured to generate, based on first analysis on a pathological slide image, first biomarker expression information, generate, based on a user input for updating at least some of results of the first analysis, second biomarker expression information about the pathological slide image, and control a display device to output a report including medical information about at least some regions included in the pathological slide image, based on at least one of the first biomarker expression information or the second biomarker expression information.

16 Claims, 23 Drawing Sheets

FIG. 1
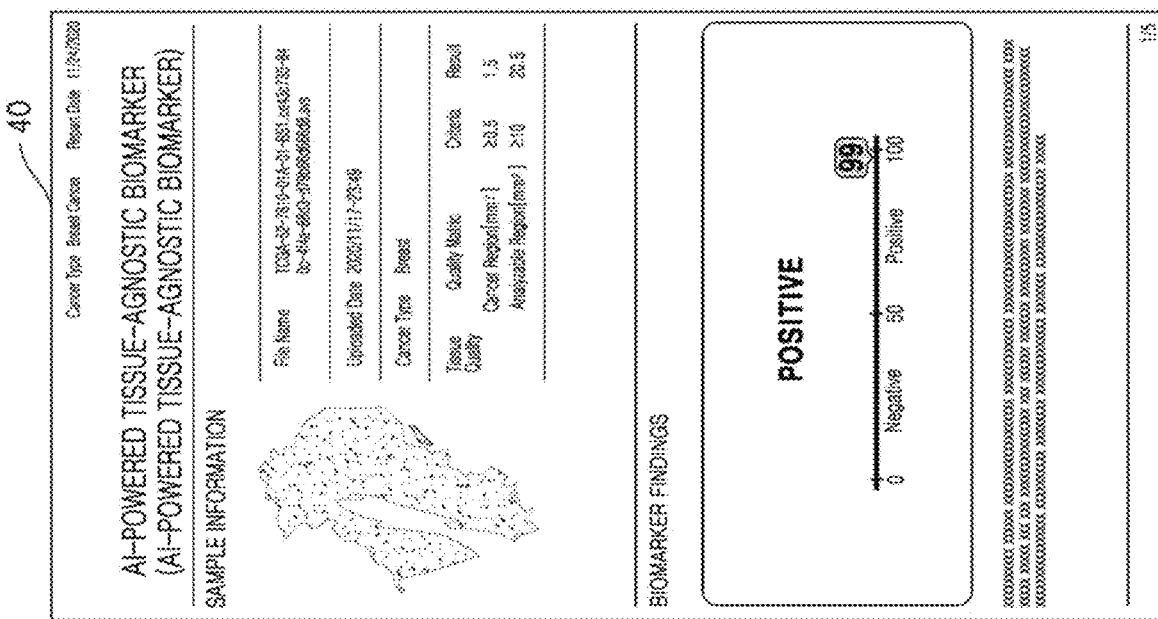
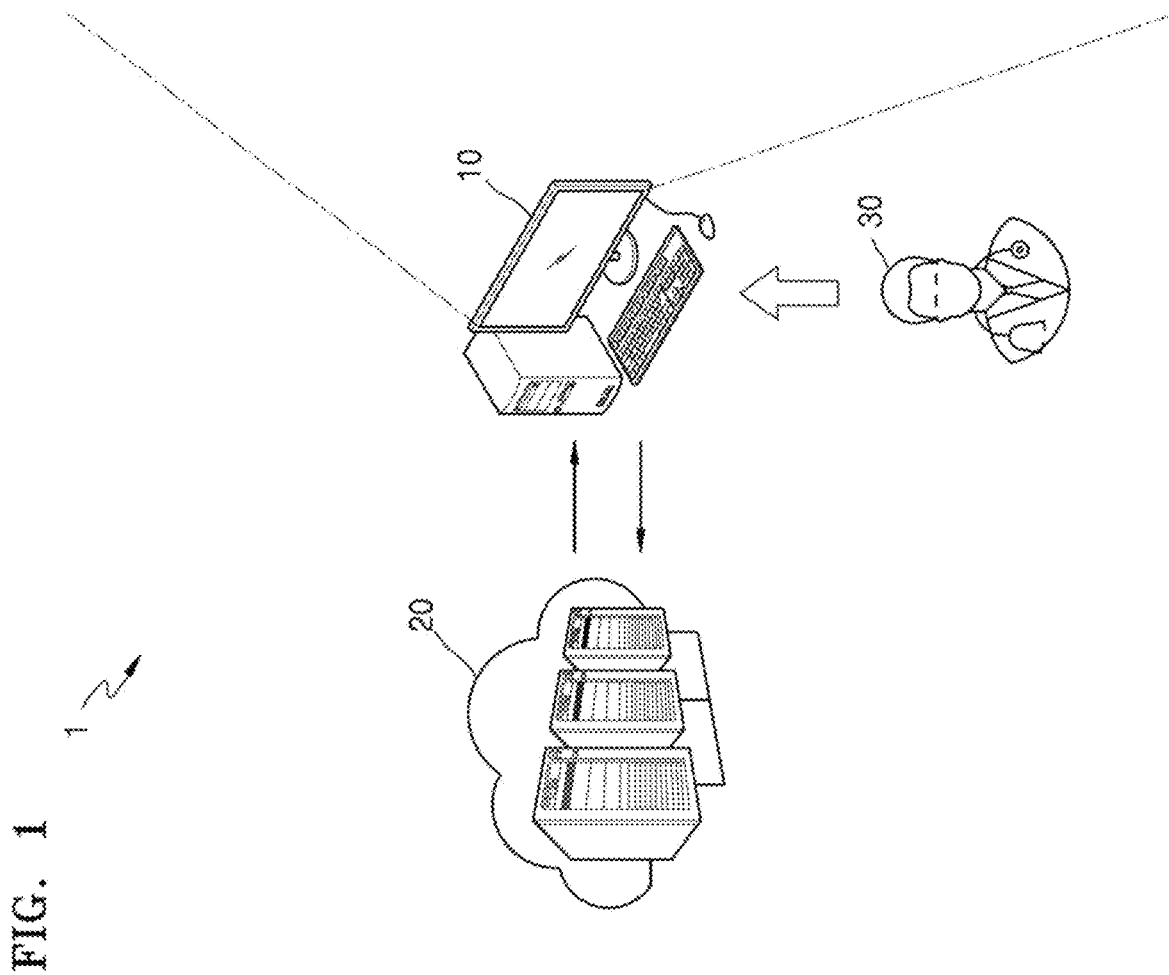

ized Patent Applications No. 10-2022-0033928, filed on Mar. 18, 2022, and No. 10-2022-0156241, filed on Nov. 21, 2022, in the Korean Intellectual Property Office, the disclosure of which is incorporated by reference herein in its entirety.

METHOD AND DEVICE FOR PROCESSING PATHOLOGICAL SLIDE IMAGE

CROSS-REFERENCE TO RELATED APPLICATION

This application is based on and claims priority under 35 U.S.C. § 119 to Korean Patent Applications No. 10-2022-0033928, filed on Mar. 18, 2022, and No. 10-2022-0156241, filed on Nov. 21, 2022, in the Korean Intellectual Property Office, the disclosure of which is incorporated by reference herein in its entirety.

BACKGROUND

1. Field

The disclosure relates to a method and device for processing a pathological slide image.

2. Description of the Related Art

The field of digital pathology refers to a field of obtaining histological information or predicting a prognosis of a subject by using a whole slide image generated by scanning a pathological slide image.

The pathological slide image may be obtained from a stained tissue sample of the subject. For example, a tissue sample may be stained by various staining methods, such as hematoxylin and eosin, trichrome, periodic acid-Schiff, autoradiography, enzyme histochemistry, immunofluorescence, and immunohistochemistry. The stained tissue sample may be used for histology and biopsy evaluations, and thus may operate as a basis for determining whether or not to move on to molecular profile analysis to understand a disease state.

A result of detecting or segmenting biological elements from the pathological slide image may be an input for biomarker analysis. However, in a case in which the performance of a machine learning model for detecting or segmenting biological elements from a pathological slide image is low, biomarker analysis may be adversely affected, which may be an obstacle to establishing an accurate treatment plan for a subject.

SUMMARY

Provided are a method and device for processing a pathological slide image. Provided is a computer-readable recording medium having recorded thereon a program for executing the method on a computer. The objects to be achieved are not limited to the objects as described above, and other objects may be obtained.

Additional aspects will be set forth in part in the description which follows and, in part, will be apparent from the description, or may be learned by practice of the presented embodiments of the disclosure.

According to an aspect of the disclosure, a computing device includes at least one memory, and at least one processor configured to generate, based on first analysis on a pathological slide image, first biomarker expression information, generate, based on a user input for updating at least some of results of the first analysis, second biomarker expression information about the pathological slide image, and control a display device to output a report including medical information about at least some regions included in the pathological slide image, based on at least one of the first biomarker expression information or the second biomarker expression information.

According to another aspect of the disclosure, a method of processing a pathological slide image includes generating, based on first analysis on the pathological slide image, first biomarker expression information, generating, based on a user input for updating at least some of results of the first analysis, second biomarker expression information about the pathological slide image, and outputting a report including medical information about at least some regions included in the pathological slide image, based on at least one of the first biomarker expression information or the second biomarker expression information.

According to another aspect of the disclosure, a computer-readable recording medium includes a recording medium recording thereon a program for causing a computer to execute the above-described method.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 1 is a diagram for describing an example of a system for outputting information about a pathological slide image, according to some embodiments;

DETAILED DESCRIPTION

Figure 2:
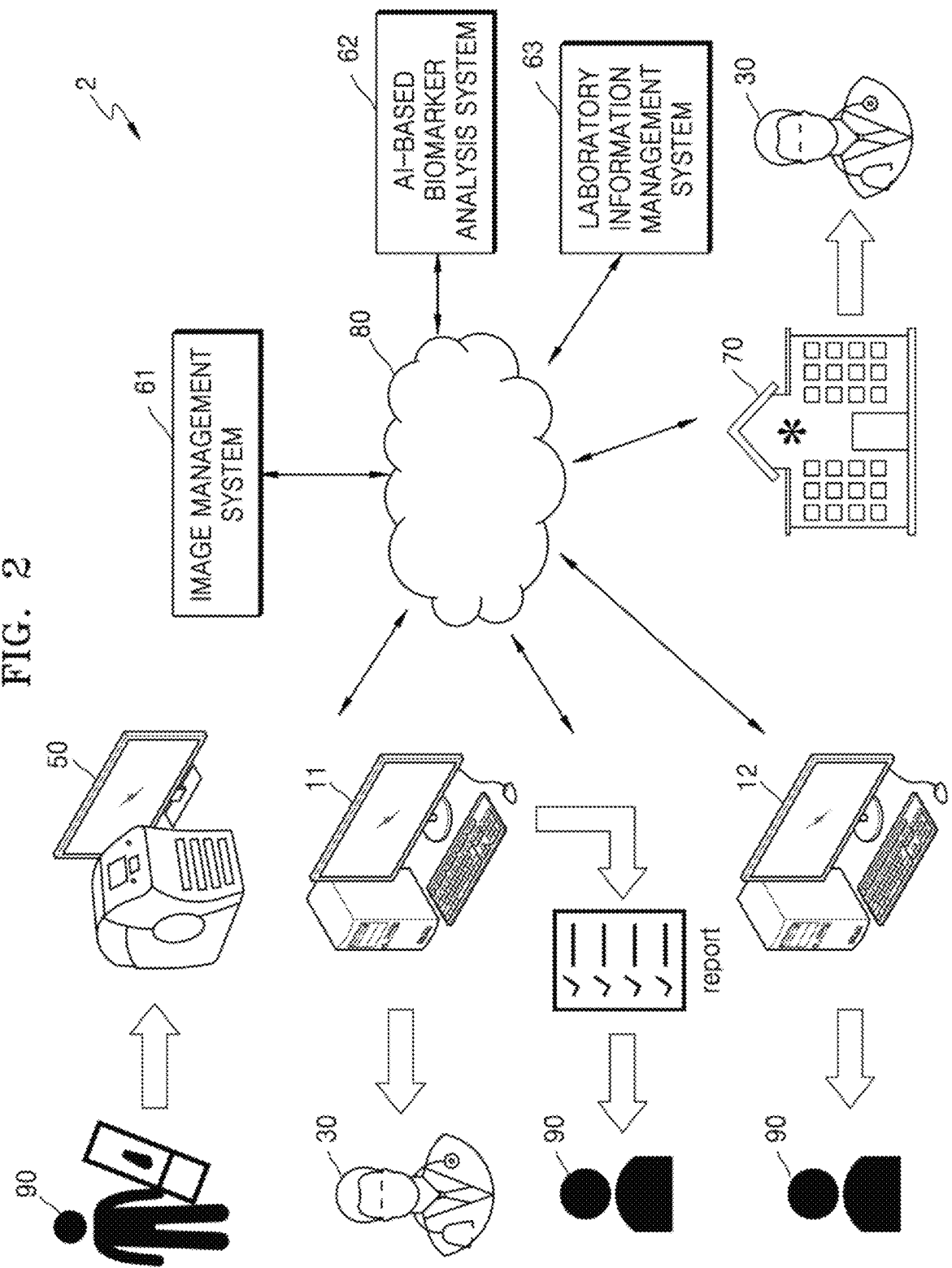
FIG. 2 is a block diagram of a system and a network for preparing, processing, and reviewing slide images of tissue specimens by using machine learning, according to some embodiments.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Terms used in embodiments are selected as currently widely used general terms as possible, which may vary depending on intentions or precedents of one of ordinary skill in the art, emergence of new technologies, and the like. In addition, in certain cases, there are also terms arbitrarily selected by the applicant, and in this case, the meaning thereof will be defined in detail in the description. Therefore, the terms used herein should be defined based on the meanings of the terms and the details throughout the description, rather than the simple names of the terms.

Throughout the present specification, when a part "includes" a component, it means that the part may additionally include other components rather than excluding other components as long as there is no particular opposing recitation. In addition, the term, such as "~unit" or "~module" described herein, refers to a unit that processes at least one function or operation, which may be implemented as hardware or software, or a combination of hardware and software.

In addition, although the terms such as "first" or "second" may be used herein to describe various elements, these elements should not be limited by these terms. These terms may be only used to distinguish one element from another.

According to some embodiments, a "pathological slide image" may refer to an image obtained by photographing a pathological slide that is fixed and stained via a series of chemical treatment processes for tissue or the like removed from a human body. In addition, the pathological slide image may refer to a whole slide image (WSI) including a high-resolution image of a whole slide, and may also refer to a portion of the whole slide image, for example, one or more patches. For example, the pathological slide image may refer to a digital image captured or scanned via a scanning apparatus (e.g., a digital scanner or the like), and may include information regarding a particular protein, cell, tissue and/or structure within a human body. In addition, a pathological slide image may include one or more patches, and histological information may be applied (e.g., tagged) to the one or more patches via an annotation operation.

According to some embodiments, "medical information" may refer to any medically meaningful information that may be extracted from a medical image, and may include, for example, an area, location, and size of a tumor cell within a medical image, diagnostic information regarding cancer, information associated with a subject's possibility of developing cancer, and/or a medical conclusion associated with cancer treatment, but is not limited thereto. In addition, the medical information may include not only a quantified numerical value that may be obtained from a medical image, but also information obtained by visualizing the numerical value, predictive information according to the numerical value, image information, statistical information, and the like. The medical information generated as described above may be provided to a user terminal or output or transmitted to a display device to be displayed.

Hereinafter, embodiments will be described in detail with reference to the accompanying drawings. The embodiments may, however, be embodied in many different forms and should not be construed as being limited to the embodiments set forth herein.

FIG. 1 is a diagram for describing an example of a system for outputting information about a pathological slide image, according to some embodiments.

Referring to FIG. 1, a system 1 includes a user terminal 10 and a server 20. For example, the user terminal 10 and the server 20 may be connected to each other by a wired or wireless communication method to transmit and/or receive data (e.g., image data or the like) to and/or from each other.

For convenience of description, FIG. 1 illustrates that the system 1 includes the user terminal 10 and the server 20, but is not limited thereto. For example, other external devices (not shown) may be included in the system 1, and operations of the user terminal 10 and the server 20 to be described below may be implemented by a single device (e.g., the user terminal 10 or the server 20) or more devices.

The user terminal 10 may be a computing device that is provided with a display device and a device (e.g., a keyboard, a mouse, or the like) for receiving a user input, and includes a memory and a processor. For example, the user terminal 10 may correspond to a notebook personal computer (PC), a desktop PC, a laptop, a tablet computer, a smart phone, or the like, but is not limited thereto.

The server 20 may be a device that communicates with an external device such as the user terminal 10. For example, the server 20 may be a device that stores various types of data including a pathological slide image, a bitmap image corresponding to a pathological slide image, information generated by analysis of a pathological slide image (e.g., information about at least one tissue and cell expressed in the pathological slide image, biomarker expression information, etc.). The server 20 may be a computing device including a memory and a processor, and having a computing capability. In a case in which the server 20 is a computing device, the server 20 may perform at least some of operations of the user terminal 10 to be described below with reference to FIGS. 1 to 22. For example, the server 20 may also be a cloud server, but is not limited thereto.

The user terminal 10 outputs an image 40 representing information generated through analysis of a pathological slide image and/or a pathological slide. For example, various pieces of information about at least one tissue and cell expressed in the pathological slide image may be expressed in the image 40. In addition, biomarker expression information may be expressed in the image 40. In addition, the image 40 may be a report including medical information about at least some regions included in the pathological slide image. Detailed examples of tissue and cell information, biomarker expression information, and reports that may be output as the image 40 will be described below.

The pathological slide image may refer to an image obtained by photographing a pathological slide that is fixed and stained through a series of chemical treatment processes to observe, with a microscope, a tissue or the like removed from a human body. For example, the pathological slide image may refer to a whole slide image including a high-resolution image of a whole slide. As another example, the pathological slide image may refer to a part of the high-resolution whole slide image.

Meanwhile, the pathological slide image may refer to a patch region obtained by dividing the whole slide image into patch units. For example, the patch may have a size of a certain area. Alternatively, the patch may refer to a region including each of objects included in the whole slide.

In addition, the pathological slide image may refer to a digital image captured by using a microscope, and may include information about cells, tissues, and/or structures in the human body.

The user terminal 10 may perform analysis on the pathological slide image and generate first biomarker expression information based on the analysis. In addition, the user terminal 10 may generate second biomarker expression information about the pathological slide image based on a user input for updating at least some of analysis results. Also, the user terminal 10 may output a report including medical information about at least some regions included in the pathological slide image, based on the first biomarker expression information and/or the second biomarker expression information.

Here, the analysis of the pathological slide image and the generation of the biomarker expression information may be performed by a machine learning model. For example, a first machine learning model for analyzing a pathological slide image and the third machine learning model for generating biomarker expression information may be different machine learning models. As another example, a machine learning model for analyzing a pathological slide image and a machine learning model for generating biomarker expression information may be the same as each other.

The analysis results on the pathological slide image may be used as input data for biomarker analysis. If the performance of a machine learning model for detecting or segmenting biological elements from a pathological slide image is low, or if the quality of a result output from the machine learning model is poor, the quality of the biomarker analysis (i.e., the quality of the biomarker expression information) is directly adversely affected, which may be an obstacle to accurately establishing a treatment plan for a subject.

In this regard, a user 30 may update (e.g., add, delete, or modify) the analysis results on the pathological slide image before biomarker analysis is performed or before the update of previously performed biomarker analysis. Here, the updating by the user 30 may be performed for at least a part of the pathological slide image. In other words, the user 30 may update all or part of the analysis results on the pathological slide image.

One pathological slide image (or a particular region of interest in the image) is composed of a significantly large number of pixels, and the size of the image is large enough to express hundreds of thousands to tens of millions of cells. Accordingly, it may be difficult for the user 30 to update all erroneous analysis results on the entire pathological slide image.

According to some embodiments, the user terminal 10 may generate biomarker expression information about the pathological slide image, based on a user input from the user 30 for updating at least some of the analysis results on the pathological slide image. Accordingly, even in a case in which the performance of the machine learning model for analyzing a pathological slide image is low or the quality of a result output from the machine learning model is poor, biomarker expression information may be accurately generated.

In addition, even in a case in which the user 30 updates only some of the analysis results on the pathological slide image, the user terminal 10 may update all of the analysis results on the pathological slide image. Accordingly, the biomarker expression information in the pathological slide image may be accurately generated.

In other words, the user terminal 10 may accurately generate the biomarker expression information even in a case in which there is an error in at least some of the analysis results on the pathological slide image. Accordingly, the report generated by the user terminal 10 may include a basis for establishing an accurate treatment plan for the subject.

Meanwhile, for convenience of description, throughout the present specification, it is described that the user terminal 10 generates the first biomarker expression information based on the analysis on the pathological slide image, generates the second biomarker expression information based on a user input, and output the report based on at least one of the first biomarker expression information or the second biomarker expression information, but the disclosure is not limited thereto. For example, at least some of operations performed by the user terminal 10 may also be performed by the server 20.

In other words, at least some of operations of the user terminal 10 described with reference to FIGS. 1 to 22 may be performed by the server 20. For example, the server 20 may generate the first biomarker expression information by analyzing the pathological slide image. In addition, the server 20 may generate the second biomarker expression information based on a user input transmitted from the user terminal 10. Also, the server 20 may generate the report based on at least one of the first biomarker expression information and the second biomarker expression information, and transmit the generated report to the user terminal 10. However, the operation of the server 20 is not limited to that described above.

FIG. 2 is a block diagram of a system and a network for preparing, processing, and reviewing slide images of tissue specimens by using machine learning, according to some embodiments.

Referring to FIG. 2, a system 2 includes user terminal(s) 11 and/or 12, a scanner 50, an image management system 61, an artificial intelligence (AI)-based biomarker analysis system 62, a laboratory information management system 63, and a server 70. In addition, the components (11, 12, 50, 61, 62, 63, and 70) included in the system 2 may be connected to each other through a network 80. For example, the network 80 may be a network through which the components (11, 12, 50, 61, 62, 63, and 70) may be connected to each other in a wired or wireless communication method. For example, the system 2 illustrated in FIG. 2 may include a network that may be connected to servers in hospitals, research facilities, laboratories, and the like, and/or user terminals of doctors or researchers.

According to various embodiments of the disclosure, methods to be described below with reference to FIGS. 3A to 22 may be performed by the user terminal(s) 11 and/or 12, the image management system 61, the AI-based biomarker analysis system 62, the laboratory information management system 63, and/or the hospital or laboratory server 70.

The scanner 50 may obtain a digitized image from a tissue sample slide generated by using a tissue sample of a subject 90. For example, the scanner 50, the user terminal(s) 11 and/or 12, the image management system 61, the AI-based biomarker analysis system 62, the laboratory information management system 63, and/or the hospital or laboratory server 70 may be connected to the network 80, such as the Internet, through one or more computers, servers, and/or mobile devices, respectively, or may communicate with the user 30 and/or the subject 90 through one or more computers, and/or mobile devices.

The user terminal(s) 11 and/or 12, the image management system 61, the AI-based biomarker analysis system 62, the laboratory information management system 63, and/or the hospital or laboratory server 70 may generate or otherwise obtain, from another device, one or more tissue samples of the subject 90, a tissue sample slide, digitized images of the tissue sample slide, or any combination thereof. In addition, the user terminal(s) 11 and/or 12, the image management system 61, the AI-based biomarker analysis system 62, and the laboratory information management system 63 may obtain any combination of subject-specific information, such as age, medical history, cancer treatment history, family history, and past biopsy records of the subject 90, or disease information of the subject 90.

The scanner 50, the user terminal(s) 11 and/or 12, the image management system 61, the laboratory information management system 63, and/or the hospital or laboratory server 70 may transmit digitized slide images and/or subject-specific information to the AI-based biomarker analysis system 62 through the network 80.

The AI-based biomarker analysis system 62 may include one or more storage devices (not shown) for storing images and data received from at least one of the scanner 50, the user terminal(s) 11 and/or 12, the image management system 61, the laboratory information management system 63, and/or the hospital or laboratory server 70. In addition, the AI-based biomarker analysis system 62 may include a machine learning model repository that stores a machine learning model trained to process the received images and data. For example, the AI-based biomarker analysis system 62 may include a machine learning model that is trained to predict, from a pathological slide image of the subject 90, at least one of information about at least one cell, information about at least one region, information related to a biomarker, medical diagnostic information, and/or medical treatment information.

The scanner 50, the user terminal(s) 11 and/or 12, the AI-based biomarker analysis system 62, the laboratory information management system 63, and/or the hospital or laboratory server 70 may transmit, to the image management system 61 through the network 80, a digitized slide image, subject-specific information, and/or a result of analyzing the digitized slide image. The image management system 61 may include a repository for storing received images and a repository for storing analysis results.

In addition, according to various embodiments of the disclosure, a machine learning model that is trained to predict, from a slide image of the subject 90, at least one of information about at least one cell, information about at least one region, information related to a biomarker, medical diagnostic information, and/or medical treatment information, may be stored in the user terminal(s) 11 and/or 12 and/or the image management system 61 and operate.

According to various embodiments of the disclosure, a method of analyzing a pathological slide image, a method of processing subject information, a method of selecting a subject group, a method of designing a clinical trial, a method of generating biomarker expression information, and/or a method of setting a reference value for a particular biomarker may be performed not only by the AI-based biomarker analysis system 62, but also by the user terminal(s) 11 and/or 12, the image management system 61, the laboratory information management system 63 and/or the hospital or laboratory server 70.

Figure 3A:
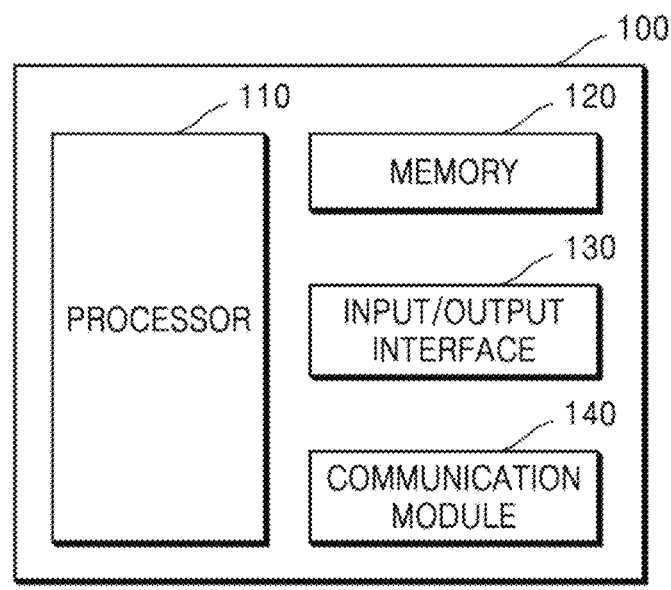
FIG. 3A is a block diagram illustrating an example of a user terminal according to some embodiments.

FIG. 3A is a block diagram illustrating an example of a user terminal according to some embodiments.

Referring to FIG. 3A, a user terminal 100 includes a processor 110, a memory 120, an input/output interface 130, and a communication module 140. For convenience of description, FIG. 3A illustrates only components related to the disclosure. Accordingly, the user terminal 100 may further include other general-purpose components, in addition to the components illustrated in FIG. 3A. In addition, it is obvious to those of skill in the art related to the disclosure that the processor 110, the memory 120, the input/output interface 130, and the communication module 140 illustrated in FIG. 3A may also be implemented as independent devices.

In addition, the operation of the user terminal 100 may be performed by the user terminal(s) 11 and/or 12, the image management system 61, the AI-based biomarker analysis system 62, the laboratory information management system 63, and/or the hospital or laboratory server 70 of FIG. 2.

The processor 110 may process commands of a computer program by performing basic arithmetic, logic, and input/output operations. Here, the commands may be provided from the memory 120 or an external device (e.g., the server 20, etc.). In addition, the processor 110 may control the overall operation of other components included in the user terminal 100.

The processor 110 may generate first biomarker expression information based on first analysis on a pathological slide image. For example, the processor 110 may identify information about at least one tissue and cell expressed in the pathological slide image, and generate the first biomarker expression information based on the identified information.

In this case, the first analysis may be performed by a first machine learning model, and second analysis to be described below may be performed by a second machine learning model. Here, the second machine learning model may be the same model as the first machine learning model, or may be a model obtained by updating the first machine learning model. For example, the second machine learning model may be a model obtained by training the first machine learning model based on information obtained by modifying results of the first analysis according to a user input.

Meanwhile, generation of the first biomarker expression information may be performed by a third machine learning model. In addition, generation of second biomarker expression information to be described below may also be performed by the third machine learning model.

The processor 110 may generate second biomarker expression information about the pathological slide image based on a user input for updating at least some of the results of the first analysis. For example, the processor 110 may perform second analysis on the pathological slide image based on a user input, and generate second biomarker expression information based on the second analysis.

The user input may be to modify or delete at least some of the results of the first analysis or to add information not included in the results of the first analysis. For example, the user 30 may check the results of the first analysis according to priorities that are set based on the first biomarker expression information, and then generate a user input for updating at least some of the results of the first analysis.

The processor 110 may generate a report including medical information about at least some regions included in the pathological slide image, based on at least one of the first biomarker expression information or the second biomarker expression information. Then, the processor 110 may control a display device to output the report.

For example, the report may include at least one of the first biomarker expression information, the second biomarker expression information, medical information based on at least one selected from among the first biomarker expression information and the second biomarker expression information, and medical information based on a result of comparing the first biomarker expression information with the second biomarker expression information.

Meanwhile, the processor 110 may verify the pathological slide image before performing the first analysis on the pathological slide image, and perform anonymization on subject-identifiable information, among information corresponding to the pathological slide image. For example, the processor 110 may perform at least one of first verification on a staining method corresponding to the pathological slide image, second verification on metadata corresponding to the pathological slide image, or third verification on an image pyramid corresponding to the pathological slide image.

In addition, the processor 110 may control the display device to output the results of the first analysis and the first biomarker expression information. Also, the processor 110 may control the display device to output the second biomarker expression information.

The processor 110 may be implemented as an array of a plurality of logic gates, or may be implemented as a combination of a general-purpose microprocessor and a memory storing a program executable by the microprocessor. For example, the processor 110 may include a general-purpose processor, a central processing unit (CPU), a microprocessor, a digital signal processor (DSP), a controller, a microcontroller, a state machine, etc. In some environments, the processor 110 may include an application-specific integrated circuit (ASIC), a programmable logic device (PLD), a field-programmable gate array (FPGA), etc. For example, processor 110 may refer to a combination of processing devices, such as a combination of a DSP and a microprocessor, a combination of a plurality of microprocessors, a combination of one or more microprocessors combined with a DSP core, or a combination of any other such configurations.

The memory 120 may include any non-transitory computer-readable recording medium. For example, the memory 120 may include a permanent mass storage device, such as random-access memory (RAM), read-only memory (ROM), a disk drive, a solid-state drive (SSD), or flash memory. As another example, the permanent mass storage device, such as ROM, an SSD, flash memory, or a disk drive, may be a permanent storage device separate from the memory. Also, the memory 120 may store an operating system (OS) and at least one piece of program code (e.g., code for the processor 110 to perform an operation to be described below with reference to FIGS. 4 to 22).

These software components may be loaded from a computer-readable recording medium separate from the memory 120. The separate computer-readable recording medium may be a recording medium that may be directly connected to the user terminal 100, and may include, for example, a computer-readable recording medium, such as a floppy drive, a disk, a tape, a digital video disc (DVD)/compact disc ROM (CD-ROM) drive, or a memory card. Alternatively, the software components may be loaded into the memory 120 through the communication module 140 rather than a computer-readable recording medium. For example, at least one program may be loaded to the memory 120 based on a computer program (e.g., a computer program for the processor 110 to perform an operation to be described below with reference to FIGS. 4 to 22) installed by files provided by developers or a file distribution system that provides an installation file of an application, through the communication module 140.

The input/output interface 130 may be a unit for an interface with a device (e.g., a keyboard or a mouse) for input or output that may be connected to the user terminal 100 or included in the user terminal 100. Although FIG. 3A illustrates that the input/output interface 130 is an element implemented separately from the processor 110, the disclosure is not limited thereto, and the input/output interface 130 may be implemented to be included in the processor 110.

The communication module 140 may provide a configuration or function for the server 20 and the user terminal 100 to communicate with each other through a network. In addition, the communication module 140 may provide a configuration or function for the user terminal 100 to communicate with another external device. For example, a control signal, a command, data, and the like provided under control by the processor 110 may be transmitted to the server 20 and/or an external device through the communication module 140 and a network.

Meanwhile, although not illustrated in FIG. 3A, the user terminal 100 may further include a display device. Alternatively, the user terminal 100 may be connected to an independent display device in a wired or wireless communication manner to transmit and receive data to and from each other. For example, a pathological slide image, a report, analysis information of the pathological slide image, biomarker expression information, and the like may be provided to the user 30 through the display device.

Figure 3B:
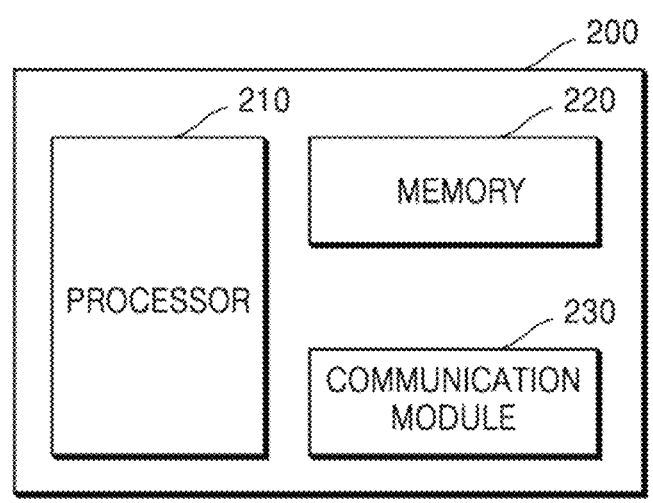
FIG. 3B is a configuration diagram illustrating an example of a server according to some embodiments.

FIG. 3B is a configuration diagram illustrating an example of a server according to some embodiments.

Referring to FIG. 3B, a server 200 includes a processor 210, a memory 220, and a communication module 230. For convenience of description, FIG. 3B illustrates only components related to the disclosure. Accordingly, the server 200 may further include other general-purpose components, in addition to the components illustrated in FIG. 3B. In addition, it is obvious to those of skill in the art related to the disclosure that the processor 210, the memory 220, and the communication module 230 illustrated in FIG. 3B may also be implemented as independent devices.

The processor 210 may obtain a pathological slide image from at least one of the memory 220, an external memory (not shown), the user terminal 100, or an external device. The processor 210 may generate first biomarker expression information based on first analysis on the pathological slide image, generate second biomarker expression information about the pathological slide image based on a user input for updating at least some of results of the first analysis, or generate a report including medical information about at least some regions included in the pathological slide image, based on at least one of the first biomarker expression information or the second biomarker expression information. In addition, the processor 210 may verify the pathological slide image or perform anonymization on subject-identifiable information among information corresponding to the pathological slide image, before performing the first analysis on the pathological slide image.

In other words, at least one of the operations of the processor 110 described above with reference to FIG. 3A may be performed by the processor 210. In this case, the user terminal 100 may output, through a display device, information transmitted from the server 200.

Meanwhile, an implementation example of the processor 210 is the same as that of the processor 110 described above with reference to FIG. 3A, and thus, detailed descriptions thereof will be omitted.

The memory 220 may store various types of data, such as a pathological slide image or data generated according to an operation of the processor 210. Also, the memory 220 may store an OS and at least one program (e.g., a program required for the processor 210 to operate, or the like).

Meanwhile, an implementation example of the memory 220 is the same as that of the memory 120 described above with reference to FIG. 3A, and thus, detailed descriptions thereof will be omitted.

The communication module 230 may provide a configuration or function for the server 200 and the user terminal 100 to communicate with each other through a network. In addition, the communication module 230 may provide a configuration or function for the server 200 to communicate with another external device. For example, a control signal, a command, data, and the like provided under control by the processor 210 may be transmitted to the user terminal 100 and/or an external device through the communication module 230 and a network.

Figure 4:
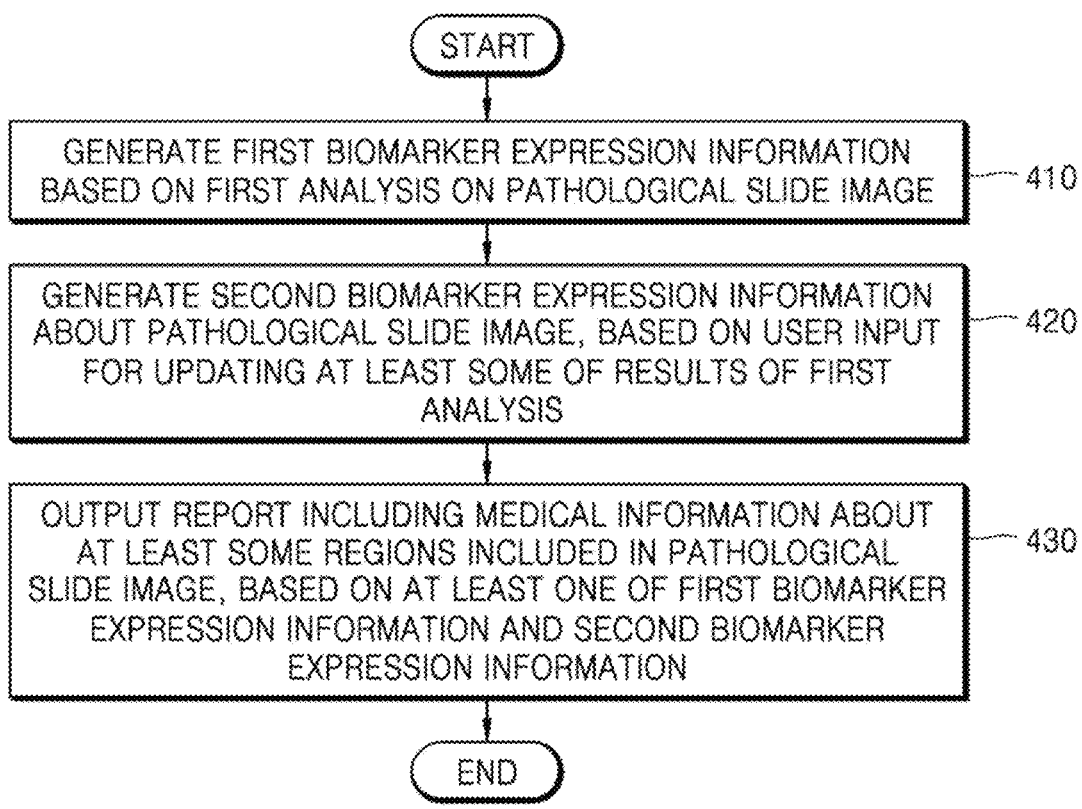
FIG. 4 is a flowchart for describing an example of a method of processing a pathological slide image according to some embodiments.

FIG. 4 is a flowchart for describing an example of a method of processing a pathological slide image according to some embodiments.

Referring to FIG. 4, the method of processing a pathological slide image includes operations that are processed, in a time-series manner, by the user terminal 10 or 100 or the processor 110 illustrated in FIGS. 1 to 3A. Therefore, the descriptions provided above with respect to the user terminal 10 or 100 or the processor 110 illustrated in FIGS. 1 and 3A, which are even omitted below, may also be applied to the method of processing a pathological slide image of FIG. 4.

In addition, as described above with reference to FIGS. 1 to 3B, at least one of operations of the flowchart illustrated in FIG. 4 may be processed by the server 20 or 200 or the processor 210.

In operation 410, the processor 110 generates first biomarker expression information based on first analysis on a pathological slide image.

First, the processor 110 performs the first analysis on the pathological slide image. Here, the first analysis on the pathological slide image may refer to analyzing tissues and/or cells in a tumor microenvironment (TME) of the pathological slide image. For example, the processor 110 may identify information about at least one tissue and/or cell expressed in the pathological slide image. Here, the information may include detecting the type and position of the tissue and/or cell.

For example, the processor 110 may perform the first analysis on the pathological slide image through a first machine learning model. A detailed example in which the processor 110 performs the first analysis will be described below with reference to FIGS. 10 and 11.

Next, the processor 110 generates the first biomarker expression information based on the information identified in the first analysis (i.e., results of the first analysis). For example, the processor 110 may generate the first biomarker expression information through a third machine learning model. A detailed example in which the processor 110 generates the first biomarker expression information will be described below with reference to FIGS. 10 and 12.

As described above, the processor 110 may perform the first analysis and generate the first biomarker expression information by using the machine learning models without intervention of the user 30. In this case, the first machine learning model for performing the first analysis and the third machine learning model for generating the first biomarker expression information may be different machine learning models or the same machine learning model.

Here, the machine learning model may refer to a statistical learning algorithm implemented based on the structure of a biological neural network, or a structure for executing the algorithm, in machine learning technology and cognitive science.

For example, the machine learning model may refer to a model having a problem solving ability by repeatedly adjusting the weights of synapses by nodes that are artificial neurons forming a network in combination with the synapses as in biological neural network, to learn such that an error between a correct output corresponding to a particular input and an inferred output is reduced. For example, the machine learning model may include an arbitrary probability model, a neural network model, etc., used in AI learning methods, such as machine learning or deep learning.

For example, the machine learning model may be implemented as a multilayer perceptron (MLP) composed of multilayer nodes and connections therebetween. The machine learning model according to some embodiments may be implemented by using one of various artificial neural network model structures including MLP. For example, a machine learning model may include an input layer that receives an input signal or data from the outside, an output layer that outputs an output signal or data corresponding to the input data, and at least one hidden layer between the input layer and the output layer to receive a signal from the input layer, extract features, and deliver the features to the output layer. The output layer receives a signal or data from the hidden layer and outputs the signal or data to the outside.

Thus, the machine learning model may be trained to receive one or more pathological slide images and extract features of one or more objects (e.g., cells, objects, structures, etc.) included in the pathological slide images. Alternatively, the machine learning model may be trained to receive one or more pathological slide images and detect tissue regions in the pathological slide images.

Although not illustrated in FIG. 4, the processor 110 may perform a certain procedure before performing the first analysis on the pathological slide image. For example, before the first analysis is performed, the processor 110 may verify the pathological slide image and perform anonymization on subject-identifiable information among information corresponding to the pathological slide image. Hereinafter, detailed examples of the procedures performed by the processor 110 before performing the first analysis will be described with reference to FIGS. 5 to 9.

Figure 5:
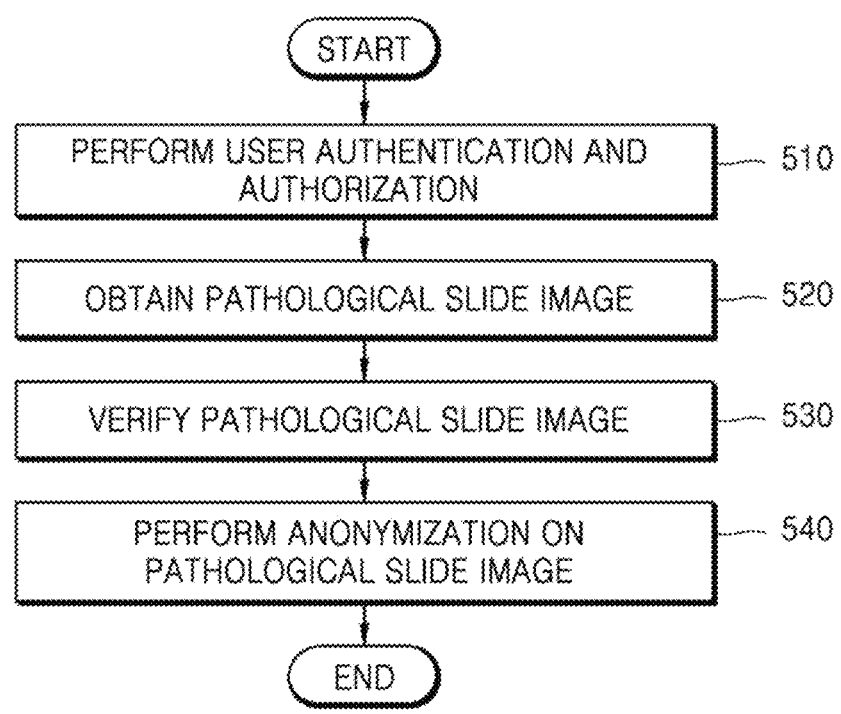
FIG. 5 is a flowchart for describing an example of procedures performed by a processor before performing first analysis, according to some embodiments.

FIG. 5 is a flowchart for describing an example of procedures performed by a processor before performing first analysis, according to some embodiments.

In operation 510, the processor 110 performs user authentication and authorization.

As the processor 110 performs a user authentication and authorization process, the user 30 may log in to the user terminal 100. Although it is described that the user 30 logs in to the user terminal 100, the disclosure is not limited thereto. In other words, the entity to which the user 30 logs in may be any device that performs the method described with reference to FIGS. 4 to 22. For example, the user 30 may log into the image management system 61, the AI-based biomarker analysis system 62, the laboratory information management system 63, or the server 70 of FIG. 2.

Here, authentication refers to a process in which the user 30 proves his/her identity, and authorization refers to an operation of granting the authenticated user 30 permission to perform a certain operation. For example, the processor 110 may perform the user authentication and authorization by using an identifier (ID), a password, an application programming interface (API) key, or the like of the user 30.

In particular, in order to enhance security of medical data, a multi-factor authentication (MFA) method may be applied to a user authentication process. Here, the MFA refers to a method of using two or more factors when authenticating the user 30.

For example, the factors may include a knowledge factor, a possession factor, and/or an inheritance factor. The knowledge factor is information that only the user knows, and may include an ID, a password, a personal identification number (PIN) code, an answer to a particular question, etc. The possession factor is information owned only by the user, and may correspond to a one-time password (OTP), a mobile phone short message service (SMS) code, a security card, etc. The inheritance factor is information according to a unique attribute of the user, and may correspond to fingerprint recognition, iris recognition, face recognition, etc.

Meanwhile, the processor 110 may perform the user authentication and authorization in different ways depending on whether the subject logging in to the user terminal 100 is the user 30 or a separate system used by the user 30. Examples in which the processor 110 performs the user authentication and authorization will be described below with reference to FIG. 6.

Figure 6:
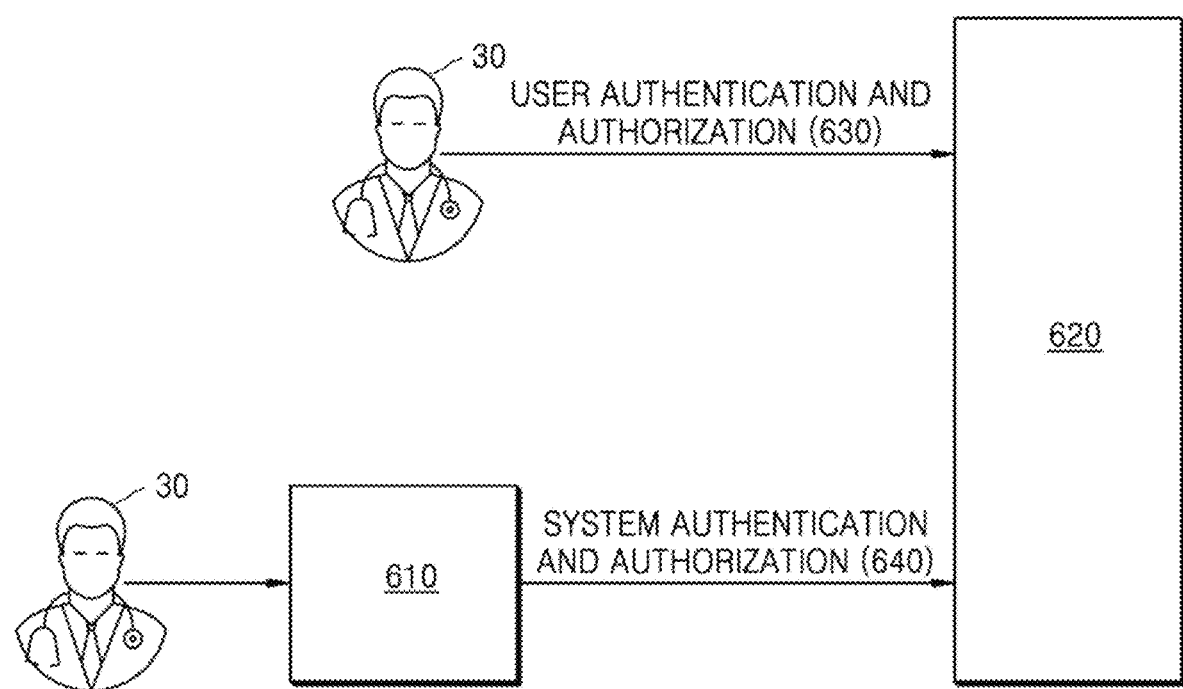
FIG. 6 is a diagram for describing examples in which a processor performs user authentication and authorization, according to some embodiments.

FIG. 6 is a diagram for describing examples in which a processor performs user authentication and authorization, according to some embodiments.

FIG. 6 illustrates a first example 630 in which the user 30 directly performs user authentication and authorization on a system 620, and a second example 640 in which the user 30 performs user authentication and authorization on the system 620 via another system 610. Here, the system 620 refers to a device or a system that performs the method described with reference to FIGS. 4 to 22. Also, the system 610 refers to a separate system of the user 30 connected to the system 620. For example, in a case in which the system 620 is the user terminal 100 of FIG. 3A, the system 610 may include a personal computing device owned by the user 30. Alternatively, in a case in which the system 620 is the server 200 of FIG. 3B, the system 610 may include the user terminal 100 of FIG. 3A or a personal computing device owned by the user 30.

For example, in the first example 630, the user 30 may utilize the functions of the system 620 after completing user authentication by using an authentication user interface (UI) provided by the system 620.

For example, in the second example 640, the system 610 may operate by integrating processes of authenticating the system 620 and the user, and the user 30 may utilize the functions of the system 620 by using the system 610.

Referring back to FIG. 5, in operation 520, the processor 110 obtains a pathological slide image.

For example, the processor 110 may read the pathological slide image from the memory 120 in the user terminal 100, or may receive the pathological slide image from an external device connected to the user terminal 100. In a case in which the user terminal 100 receives the pathological slide image from the external device, the processor 110 may store the received image in the memory 120.

The file format of the pathological slide image may vary depending on the scanner 50. The user terminal 100 may receive or store only a file format supported by the user terminal 100, among various file formats.

Meanwhile, depending on whether another system or device accessible to the user terminal 100 is provided, the processor 110 may obtain the pathological slide image in a different way. Examples in which the processor 110 obtains the pathological slide image will be described below with reference to FIG. 7.

Figure 7:
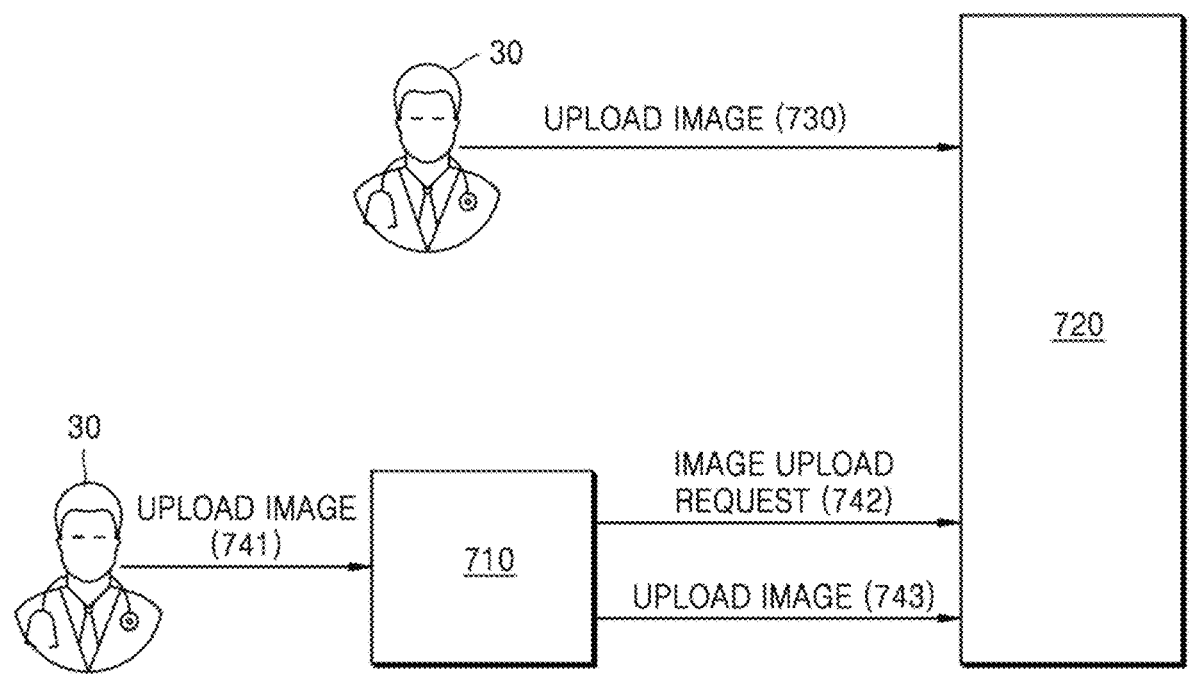
FIG. 7 is a diagram for describing examples in which a processor obtains a pathological slide image, according to some embodiments.

FIG. 7 is a diagram for describing examples in which a processor obtains a pathological slide image, according to some embodiments.

FIG. 7 illustrates a first example 730 in which a system 720 obtains a pathological slide image in a case in which another system 710 accessible to the system 720 is not provided, and a second example (741, 742, and 743) in which the system 720 obtains a pathological slide image in a case in which the other system 710 is provided. Here, the system 720 refers to a device or a system that performs the method described with reference to FIGS. 4 to 22.

Also, the system 710 refers to a separate system of the user 30 connected to the system 720. For example, assuming that the system 720 is the AI-based biomarker analysis system 62 illustrated in FIG. 2, the system 710 may correspond to the image management system 61, the laboratory information management system 63, the server 70, etc.

In the first example 730, the user 30 may command, by using a UI or an API provided by the system 720, the system 720 to upload a pathological slide image file, and the system 720 may directly upload the pathological slide image file to the system 720, based on the command of the user 30. For example, the system 720 may download (743) the pathological slide image file from the image management system 61, the laboratory information management system 63, and/or the server 70.

In the second example (741, 742, and 743), when the user 30 commands the system 710 to upload the pathological slide image file, the system 710 may access the system 720, then transmit, to the system 720, an upload request 742 for the pathological slide image file, and upload the pathological slide image file to the system 720. That is, the system 720 may download (743) the pathological slide image file from the system 710.

Referring back to FIG. 5, in operation 530, the processor 110 verifies the pathological slide image.

For example, the processor 110 may perform at least one of first verification on a staining method corresponding to the pathological slide image, second verification on metadata corresponding to the pathological slide image, or third verification on an image pyramid corresponding to the pathological slide image.

In a case in which the verification is successful, the processor 110 may perform operation 540, and in a case in which the verification fails, the processor 110 may generate an alarm notifying the user 30 that the verification on the pathological slide image has failed. Hereinafter, an example in which the processor 110 verifies a pathological slide image will be described with reference to FIG. 8.

Figure 8:
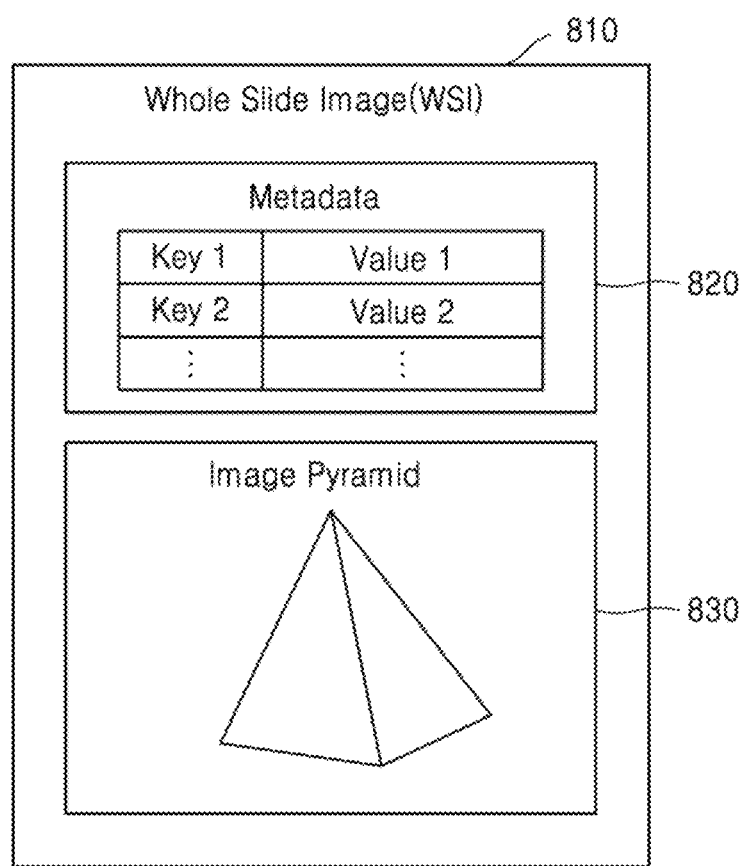
FIG. 8 is a diagram for describing an example in which a processor verifies a pathological slide image, according to some embodiments.

FIG. 8 is a diagram for describing an example in which a processor verifies a pathological slide image, according to some embodiments.

Referring to FIG. 8, a pathological slide image 810 may include metadata 820 and an image pyramid 830. The processor 110 may perform verification on each of the portions 820 and 830.

The processor 110 may perform first verification on a staining method corresponding to the pathological slide image 810. In other words, the processor 110 may verify whether the pathological slide image is well stained by a desired staining method.

For example, the processor 110 may verify the staining method of the pathological slide image based on a previously learned pathological staining method. The method by which the pathological slide image is stained may be determined based on stained colors and stained forms in which objects (e.g., cells, tissues, etc.) on the pathological slide image are stained, information related to the staining method of the pathological slide image input by the user 30, information written on a label in the pathological slide image, etc.

If the verified staining method matches a staining method to be analyzed by the user terminal 100, the next operation is performed. In a case in which the verified staining method does not match the staining method to be analyzed by the user terminal 100, this is regarded as a verification failure and the user 30 is instructed to confirm the type of the staining method, as a result of the failure of verification of the pathological slide image.

Methods of staining a pathological slide image may include hematoxylin and eosin (H&E) staining, immunohistochemical staining, special staining, immunofluorescence staining, etc. Here, representative examples of immunohistochemical staining include programmed cell death-ligand 1 (PD-L1), human epidermal growth factor receptor 2 (HER2), estrogen receptor (ER) progesterone receptor (PR), Ki-67, etc. In addition, representative examples of special staining include Van Gieson staining, Toluidine blue staining, Giemsa staining, Masson's trichrome staining, Periodic acid-Schiff staining, etc. In addition, representative examples of immunofluorescence staining include immunoglobulins, complement, fibrin, etc.

The processor 110 may perform second verification on the metadata 820 corresponding to the pathological slide image. For example, the processor 110 may verify whether information, such as physical distance information (e.g., micrometer per pixel (MPP)) between pixels included in the pathological slide image or magnification, is present in the metadata, whether the corresponding value falls within a threshold range, or the like.

The processor 110 may perform third verification on the image pyramid 830 corresponding to the pathological slide image. For example, the processor 110 may measure a total tissue image region, an image focusing out region, and the like within the pathological slide image, and verify whether the area of an analyzable tissue image region in the pathological slide image is greater than or equal to a threshold value or is within a threshold range. Here, the analyzable tissue image region may be specified by excluding, from the total tissue image region, the image focusing out region, a foreign body region, and a background image region.

Referring back to FIG. 5, in operation 540, the processor 110 performs anonymization on the pathological slide image.

The processor 110 may perform the anonymization on the pathological slide image such that the subject cannot be specified (identified) from the pathological slide image. For example, the processor 110 may delete or mask all subject-identifiable information from the pathological slide image.

Examples of subject-identifiable information in the pathological slide image are as follows. However, the subject-identifiable information in the pathological slide image is not limited to the following examples.

i) Name (title) information of a pathological slide image file: when creating the pathological slide image file after digitizing a slide, the user 30 may create the name of the pathological slide image file by using identification information of the subject.
 ii) Metadata information of the pathological slide image: when creating the pathological slide image file after digitizing the slide, the user 30 may store subject identification information in the metadata of the pathological slide image.
 iii) Label information of the pathological slide image: when digitizing the slide, the user 30 may also digitize label information of the slide. Here, the label information of the slide refers to information from which the subject may be identified in combination with other information of the subject.

For example, an example in which the processor 110 performs anonymization on a pathological slide image will be described below with reference to FIG. 9.

Figure 9:
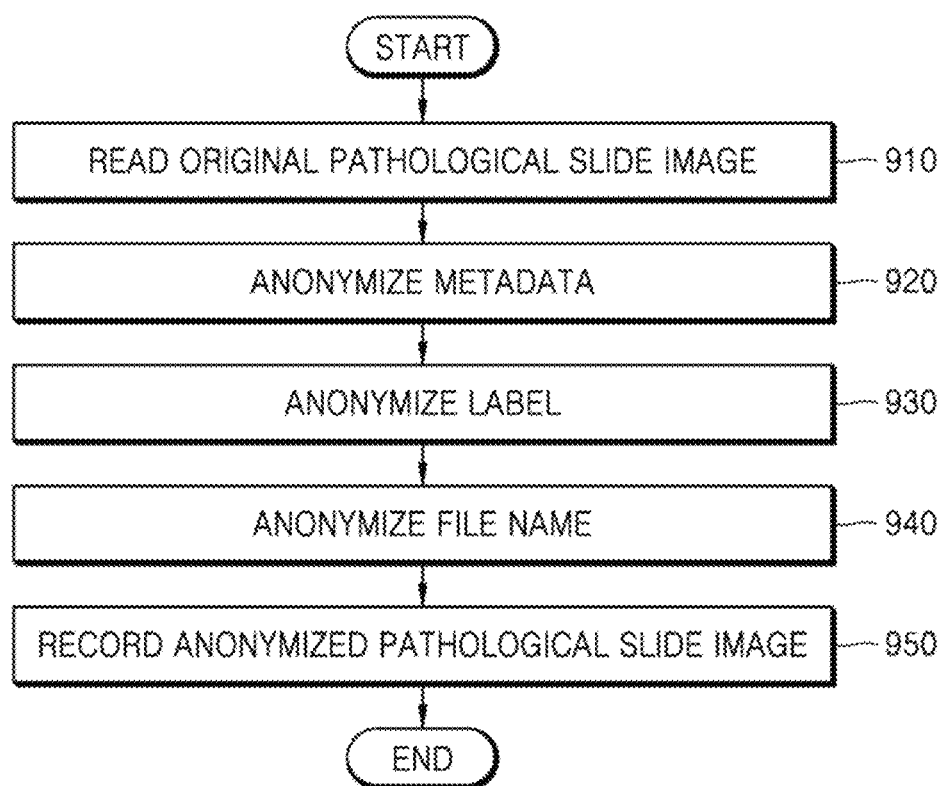
FIG. 9 is a flowchart for describing an example in which a processor performs anonymization on a pathological slide image, according to some embodiments.

FIG. 9 is a flowchart for describing an example in which a processor performs anonymization on a pathological slide image, according to some embodiments.

FIG. 9 illustrates an example in which the processor 110 anonymizes a pathological slide image. Through the following operations, the processor 110 anonymizes subject-identifiable information in a pathological slide image file, such that the pathological slide image file is stored without identification information of the subject.

In operation 910, the processor 110 reads an original pathological slide image.

For example, the processor 110 may read the original pathological slide image from the memory 120, or may receive the original pathological slide image from an external device.

In operation 920, the processor 110 anonymizes metadata.

For example, the processor 110 may delete or mask (i.e. replace with meaningless random values) other information than information (e.g., MPP, etc.) necessary for actually analyzing the image, from the metadata of an original pathological slide image file.

In operation 930, the processor 110 anonymizes a label.

For example, the processor 110 determines whether a label image region including identification information of the subject is present in the original pathological slide image. In a case in which the label image region is present, the processor 110 may delete or mask (i.e., replace with a meaningless image) the label image region.

In operation 940, the processor 110 anonymizes a file name.

For example, the processor 110 may replace the name of the original pathological slide image file with an arbitrary meaningless name (e.g., a random, a universally unique ID (UUID), etc.).

In operation 950, the processor 110 records the anonymized pathological slide image.

For example, the processor 110 may store, in the pathological slide image file, information changed through operations 920 to 940. Additionally, the processor 110 may store the anonymized pathological slide image file in the memory 120, or transmit it to an external device.

The examples in which the processor 110 performs preliminary operations before performing first analysis on a pathological slide image have been described above with reference to FIGS. 6 to 9.

Hereinafter, a detailed example in which the processor 110 performs first analysis on a pathological slide image and generates first biomarker expression information based on the first analysis will be described with reference to FIGS. 10 to 12.

Figure 10:
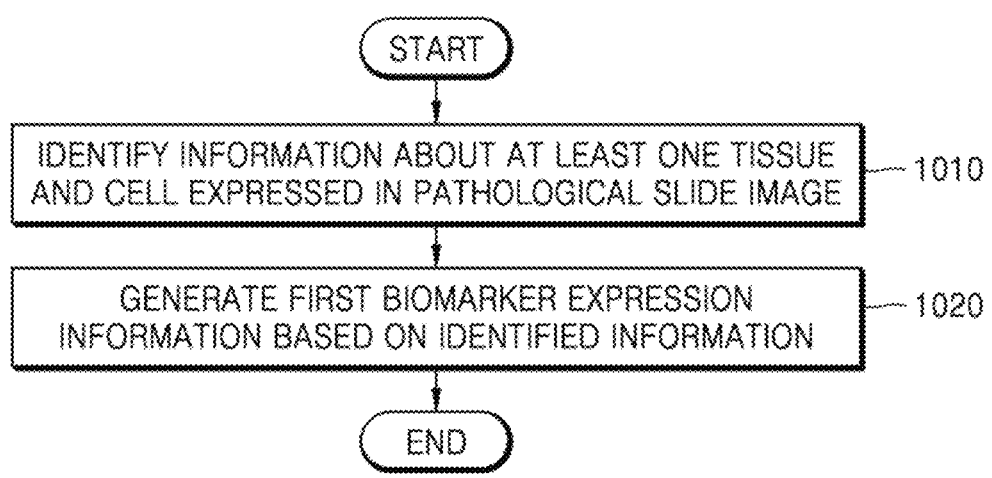
FIG. 10 is a flowchart for describing an example in which a processor performs first analysis on a pathological slide image and generates first biomarker expression information, according to some embodiments.

FIG. 10 is a flowchart for describing an example in which a processor performs first analysis on a pathological slide image and generates first biomarker expression information, according to some embodiments.

In operation 1010, the processor 110 identifies information about at least one tissue and cell expressed in the pathological slide image.

For example, the processor 110 may identify information about the tissue and cell from the pathological slide image by using the first machine learning model. Hereinafter, an example in which the processor 110 identifies, from a pathological slide image, information about tissues and cells will be described with reference to FIG. 11.

Figure 11:
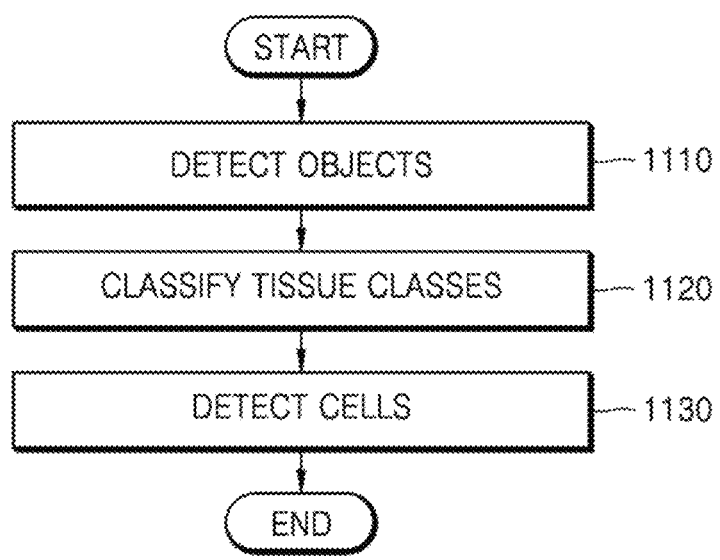
FIG. 11 is a flowchart for describing an example in which a processor identifies, from a pathological slide image, information about tissues and cells, according to some embodiments.

FIG. 11 is a flowchart for describing an example in which a processor identifies, from a pathological slide image, information about tissues and cells, according to some embodiments.

In operation 1110, the processor 110 detects at least one object from the pathological slide image.

For example, the processor 110 may detect a region of interest including an object from the pathological slide image by excluding a background region from the pathological slide image.

For example, the processor 110 may detect the region of interest by comparing a numerical value corresponding to a feature of each of a plurality of pixels included in the pathological slide image, with a threshold value. For example, the first machine learning model may be a model for detecting a region of interest in a pathological slide image by using a thresholding technique (e.g., Otsu thresholding technique, etc.) for the color and/or intensity of each of a plurality of pixels.

As another example, the processor 110 may detect the contour of at least one object included in the pathological slide image. Here, the contour detection technique may be any previously known segmentation technique. The processor 110 may detect the region of interest in the pathological slide image by using the first machine learning model. The first machine learning model may be, for example, a model employing a machine learning technique such as an active contouring technique.

As another example, the processor 110 may detect the region of interest from the pathological slide image based on comprehensive information about features, contour, and the like of the plurality of pixels included in the pathological slide image. The processor 110 may detect the region of interest by using the first machine learning model that is trained based on annotation information about regions of interest.

In operation 1120, the processor 110 classifies or separates a tissue class from a result of operation 1110.

For example, the processor 110 may classify, from the region of interest, the type of a tissue (e.g., cancer area, cancer stroma area, carcinoma in situ area, necrotic area, etc.) and the region of a tissue.

The processor 110 performs classification on at least one tissue expressed in the pathological slide image by using the first machine learning model. For example, the first machine learning model may be a model for detecting, from a pathological slide image, regions corresponding to tissues and segmenting layers representing the tissues. Also, the first machine learning model may be a model for classifying a pathological slide image into at least one of a cancer area, a cancer stroma area, a necrosis area, or other areas.

However, examples in which the processor 110 classifies at least some regions expressed in a pathological slide image are not limited to the above description. In other words, without being limited to the above-described four types of areas (i.e., cancer region, cancer stroma region, necrosis region, and other regions), the processor 110 may classify at least one region expressed in a pathological slide image into one of a plurality of categories according to various criteria. For example, at least one region expressed in the pathological slide image may be classified into a plurality of categories according to a preset criterion or a criterion set by the user 30.

In operation 1130, the processor 110 detects cells from a result of operation 1110.

For example, the processor 110 may perform classification on a plurality of cells included in the region of interest.

For example, the first machine learning model may be a model for detecting cells from a pathological slide image and segmenting layers representing the cells. Also, the first machine learning model may be a model for classifying a plurality of cells expressed in a pathological slide image into at least one of tumor cells, lymphocyte cells, or other cells.

However, examples in which cells expressed in a pathological slide image are classified through the first machine learning model are not limited to the above description. In other words, cells expressed in a pathological slide image may be grouped according to various criteria for classifying different types of cells.

Referring back to FIG. 10, in operation 1020, the processor 110 generates first biomarker expression information based on the information identified in step 1010.

For example, according to an analysis guide of each biomarker, the processor 110 may automatically quantify the expression of the biomarker and analyze the expression rate of the biomarker. The processor 110 may generate the first biomarker expression information by using the third machine learning model. Here, the third machine learning model may be the same as or different from the first machine learning model. Hereinafter, an example in which the processor 110 generates the first biomarker expression information will be described with reference to FIG. 12.

Figure 12:
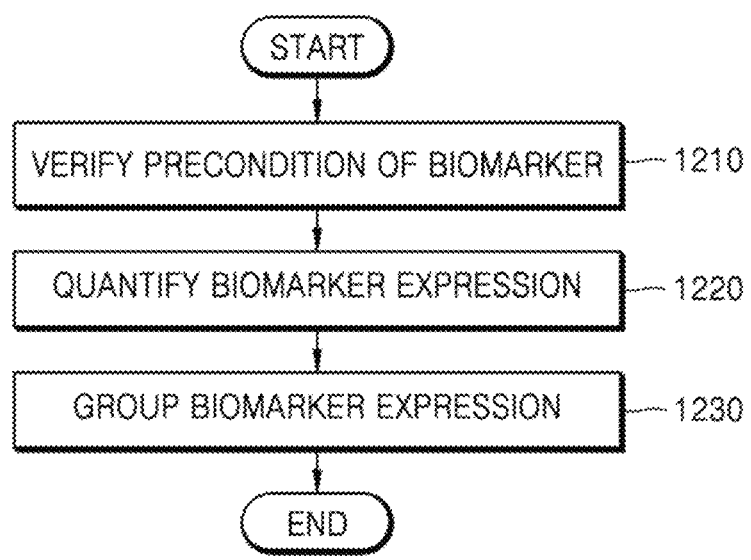
FIG. 12 is a flowchart for describing an example in which a processor generates first biomarker expression information, according to some embodiments.

FIG. 12 is a flowchart for describing an example in which a processor generates first biomarker expression information, according to some embodiments.

In operation 1210, the processor 110 verifies a precondition of a biomarker.

The processor 110 may verify the precondition before analyzing biomarker expression. However, preconditions for analyzing the expression of respective biomarkers may be different from each other. For example, in a case of 'PD-L1 22C3 PharmDx', there is a condition that the number of cancer cells needs to be 100 or more in a biomarker analysis region, but in a case of 'PD-L1 SP142', it is only necessary that the number of cancer cells is 50 or more in a biomarker analysis region. In addition, in a case of analysis of expression of a plurality of biomarkers, analysis is performed only within an invasive cancer area, and carcinoma in situ or benign tumor is often excluded from the analysis.

As described above, in a case in which the pathological slide image consists of only lesions that are not subject to analysis, the processor 110 may prevent biomarker expression analysis from being performed, through verification of the precondition.

In operation 1220, the processor 110 quantifies biomarker expression.

The processor 110 may quantify the biomarker expression by using an analysis result on the pathological slide image, according to each biomarker analysis guide. Here, the quantification method may be different for each biomarker.

For example, the processor 110 may quantify the expression level for particular staining (e.g., H&E, IHC) of a particular cell in at least some regions of the pathological slide image. For example, the processor 110 may represent, as a integer or continuous real value, the expression level of a particular class for particular staining of a particular cell in at least some regions of the pathological slide image, represent, as a percentage, the expression ratio of a particular class among all classes in at least some regions of the pathological slide image, or derive a probability value that at least some regions of the pathological slide image is of a particular class. In addition, the processor 110 may quantify the presence or absence of biomarker expression or the level of biomarker expression to derive a class value representing the immunophenotype of at least some regions of the pathological slide image, a probability value that the immunophenotype of the at least some regions is a certain class, the density of tumor-infiltrating lymphocyte (TIL), a combined positive score (CPS), and/or a tumor proportion score (TPS).

In operation 1230, the processor 110 groups biomarker expression.

The processor 110 may group the biomarker expression according to each biomarker analysis guide, based on values digitized through operation 1220. In this case, the grouping method may be different for each biomarker.

Meanwhile, although not illustrated in FIGS. 10 to 12, the processor 110 may output results of the first analysis and/or the first biomarker expression information. In other words, the processor 110 may control the display device to output the results of the first analysis and/or the first biomarker expression information.

For example, the processor 110 may overlay and output the results of the first analysis on the pathological slide image.

For example, the processor 110 may output information about a detected cell. In detail, the processor 110 may output the type of the cell and coordinates corresponding to the position of the cell in the image. For example, assuming that the coordinates of cell A are (x, y), the processor 110 may indicate cell A by overlaying on the position of (x, y) on the pathological slide image. In addition, cells may be indicated on the pathological slide image in different colors or shapes for the respective types of the cells. In addition, according to the magnification at which the user observes the pathological slide image and/or according to a manipulation by the user, the processor 110 may determine whether to indicate the cells and how to indicate the cells (e.g., the colors and sizes of the cells), and indicate the cells on the pathological slide according to a result of the determining.

In addition, the processor 110 may output information about a detected tissue. In detail, the processor 110 may output the type of the tissue and a region map. For example, in a case in which tissue B is detected, the processor 110 may indicate tissue B by overlaying the region map representing the region in which tissue B is located on the pathological slide image. In addition, tissues may be indicated on the pathological slide image in different colors or shapes for the respective types of the tissues. In addition, according to the magnification at which the user observes the pathological slide image and/or according to a manipulation by the user, the processor 110 may determine whether the tissues are indicated (i.e., indicated or not indicated), and the colors of the tissues, and indicate the tissues on the pathological slide according to a result of the determining.

As another example, the processor 110 may output the first biomarker expression information.

For example, the processor 110 may output a biomarker expression score and a biomarker expression classification. For example, the processor 110 may indicate the biomarker expression score and the biomarker expression classification separately from each other or simultaneously. The biomarker expression score may be expressed as a real number or an integer, and the biomarker expression classification may be expressed as text. Alternatively, the biomarker expression classification and the biomarker expression score may be indicated in a bar graph. In this case, the biomarker expression score may be indicated together with a cut-off value for each biomarker expression category.

In addition, the processor 110 may output the biomarker expression score map and a biomarker expression class map. For example, the score map and the class map may be overlaid and output on the pathological slide image. In this case, the biomarker expression score for each region of the pathological slide image may be output in the form of a heat map. Meanwhile, the biomarker expression class for each region of the pathological slide image may be output in the form of a map image.

As another example, regardless of the results of the first analysis and the output of the first biomarker expression information, the processor 110 may output common information.

For example, the processor 110 may output a live analyzer. For example, the processor 110 may overlay, on the pathological slide image, and output the number of cells for each type and the number of tissues for each type in a particular region (e.g., a region designated by the user 30), and/or the area of the region, in real time. In this case, the particular region may be indicated with a certain figure (e.g., a circle, a polygon, etc.), and the user 30 may set the particular region in real time by changing the shape, size, and/or position of the figure. In addition, information within a particular region may be output in the form of a tooltip.

In addition, the processor 110 may output a view controller. For example, through the view controller, the user 30 may control whether to indicate each of output factors. In other words, the user 30 may control whether to indicate each cell type and tissue type. For example, whether to indicate/not to indicate each factor is output in the form of a check box for each factor, and accordingly, the user 30 may control whether to indicate each factor through the check box.

Referring back to FIG. 4, in operation 420, the processor 110 generates second biomarker expression information about the pathological slide image, based on a user input for updating at least some of the results of the first analysis.

Here, the updating includes not only deleting or modifying, by the user 30, at least some of the results of the first analysis, but also adding information not included in the results of the first analysis. In this case, the updating by the user 30 may be performed on at least a part of the pathological slide image. In other words, the user 30 may update all of the results of the first analysis obtained by analyzing the pathological slide image, or may update some of the results of the first analysis obtained by analyzing the pathological slide image.

For example, the processor 110 may perform the second analysis on the pathological slide image based on a user input, and generate the second biomarker expression information based on the second analysis. In this case, the second analysis may be performed by the second machine learning model obtained by updating the first machine learning model.

As described above with reference to FIGS. 10 and 11, the first analysis on the pathological slide image may be performed by using the first machine learning model. Meanwhile, when a user input regarding the results of the first analysis is received, the processor 110 may train the first machine learning model based on information obtained by modifying the results of the first analysis according to a user input, and accordingly, the second machine learning model may be generated. In other words, the second machine learning model may be a result of training the first machine learning model. For example, the second machine learning model may be a model obtained by modifying some parameters of the first machine learning model according to the content of a user input.

Meanwhile, the second biomarker expression information may be generated by the third machine learning model. Here, the third machine learning model refers to the machine learning model that generates the first biomarker expression information described above with reference to FIGS. 10 and 12. The third machine learning model may be the same as or different from the first machine learning model that performs the first analysis on the pathological slide image. In other words, the first biomarker expression information and the second biomarker expression information may be generated by the same machine learning model or by different machine learning models.

Hereinafter, an example in which the processor 110 generates the second biomarker expression information based on a user input will be described with reference to FIGS. 13 to 20.

Figure 13:
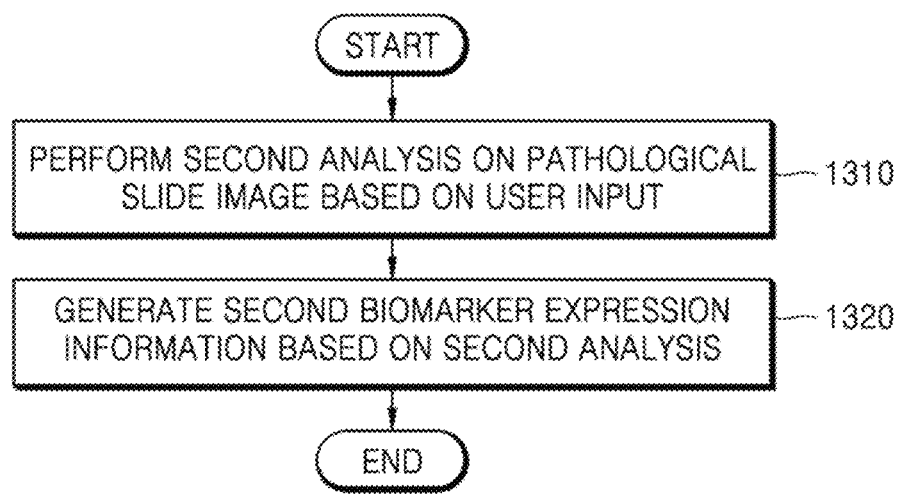
FIG. 13 is a flowchart for describing an example in which a processor receives a user input, performs second analysis, and generates second biomarker expression information, according to some embodiments.

FIG. 13 is a flowchart for describing an example in which a processor receives a user input, performs second analysis, and generates second biomarker expression information, according to some embodiments.

In operation 1310, the processor 110 performs the second analysis on the pathological slide image based on the user input.

As described above with reference to FIGS. 10 to 12, the processor 110 performs the first analysis on the pathological slide image by using the first machine learning model. However, the results of the first analysis may not be accurate depending on the performance of the first machine learning model or other circumstances.

In this regard, upon receiving a user input for updating the results of the first analysis, the processor 110 according to some embodiments performs the second analysis on the pathological slide image according to the content of the user input. In this case, the second analysis is performed by the second machine learning model. Meanwhile, the second machine learning model may be obtained by training the first machine learning model according to the content of the user input. Therefore, because errors or the like in the first analysis may be corrected through the second analysis, the accuracy of analysis of the pathological slide image may be improved.

The course of treatment of the subject may be determined according to a prediction result of a biomarker (i.e., the biomarker expression information). However, as described above, a case may occur in which the analysis results of the pathological slide image through the first machine learning model are inaccurate. For example, a detailed process of tissue staining may slightly vary depending on hospitals or subjects, which may cause differences in visual information of biological components in the pathological slide image. Accordingly, the accuracy of the analysis results of the pathological slide image through the first machine learning model may deteriorate.

In addition, visual information of biological components may be different depending on the scanner that scans a tissue of the subject, which may cause a decrease in the accuracy of analysis of the pathological slide image.

In addition, in a case in which the organ expressed in the pathological slide image is an organ that is insufficiently included in training data for the first machine learning model (e.g., stomach, lung, etc.) or is not included in the training data, the accuracy of analysis of the pathological slide image may deteriorate. Furthermore, biological components (e.g., macrophages, fibrosis cells, etc.) insufficiently included in the training data for the first machine learning model are likely to fail to be recognized by the first machine learning model.

When the accuracy of the analysis results by the first machine learning model is lowered for the reasons described above, and the low-accuracy analysis results are delivered to the third machine learning model, the accuracy of biomarker expression information generated by the third machine learning model may also be lowered. In this case, the treatment plan of the subject may be improperly established.

For example, the user input may be input after the user 30 checks the results of the first analysis according to the priorities that are set based on the first biomarker expression information. Hereinafter, an example in which the user 30 checks the results of the first analysis according to the priorities and generates a user input will be described with reference to FIGS. 14 and 15.

Figure 14:
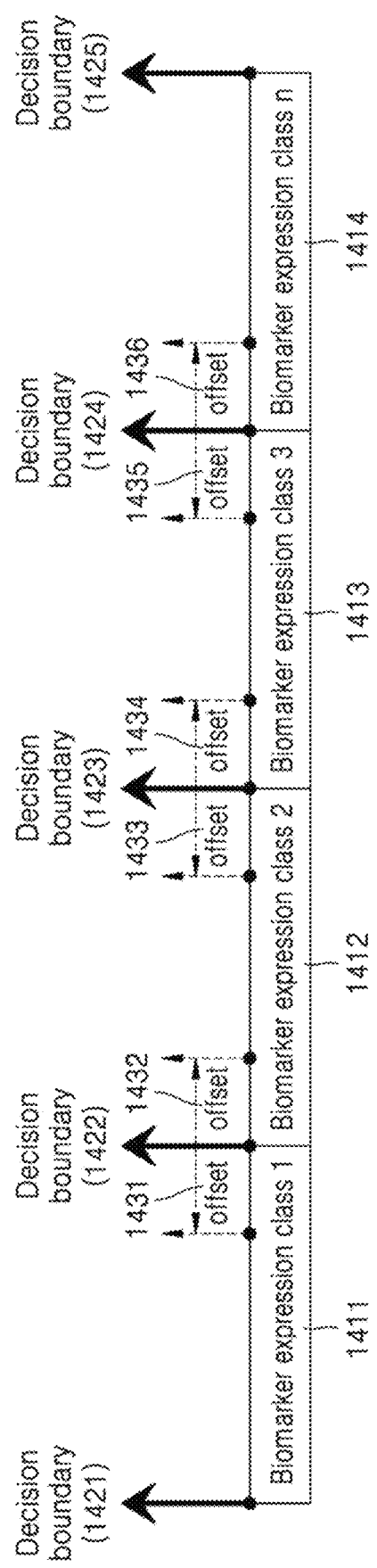
FIG. 14 is a diagram for describing an example of priorities in which a user checks results of first analysis.

FIG. 14 is a diagram for describing an example of priorities in which a user checks results of first analysis.

FIG. 14 illustrates an example in which first biomarker expression information is generated based on first analysis. In detail, biomarker expression classes 1411, 1412, 1413, and 1414 and decision boundaries 1421, 1422, 1423, 1424, and 1425 distinguishing therebetween are illustrated.

In general, it may be inefficient for the user 30 to check and reanalyze (i.e., update) the analysis results of the pathological slide image one by one. The processor 110 according to some embodiments may set priorities indicating an order of checking the pathological slide image, and the user 30 may check the analysis results of the pathological slide image according to the priorities. Accordingly, the user 30 may check and update the analysis results more efficiently.

The processor 110 may sort and output the results of the first analysis according to the priorities, and the user 30 may check and reanalyze the results of the first analysis according to the output priorities.

For example, the processor 110 may set certain offsets 1431, 1432, 1433, 1434, 1435, and 1436 from the decision boundaries 1421, 1422, 1423, 1424, and 1425, and set the priorities such that the analysis results included in the offsets 1431, 1432, 1433, 1434, 1435, and 1436 may be checked first. The user 30 may check the analysis results by sorting the priorities based on the biomarker expression information (e.g., biomarker type, score, classification, etc.).

For example, in a case of 'PD-L1 TPS', three classes ('No PD-L1', 'PD-L1', and 'High PD-L1') may be included in biomarker expression classes. Here, the classification boundaries may be classify the classes to less than 1%, 1% to 49%, and 50% or greater, respectively. The processor 110 may set an offset to 1% and set priorities for preferentially checking the analysis results present in a range of the offset based on the classification boundaries.

Meanwhile, the previously generated results of the second analysis, the second biomarker expression information, and the content of the previously received user input may be stored in the memory 120, and the processor 110 may set the priorities based on frequently modified content.

Figure 15:
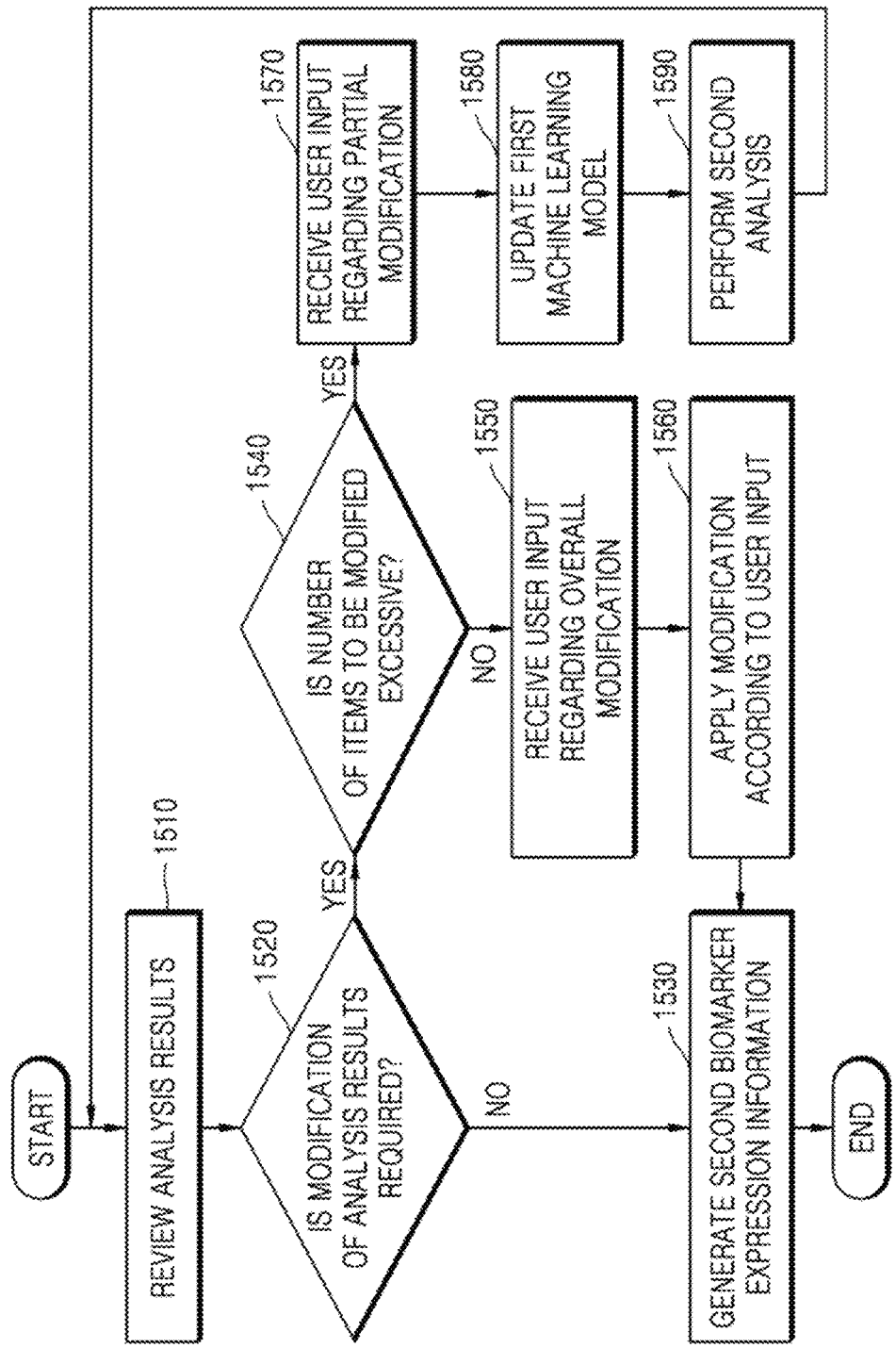
FIG. 15 is a flowchart for describing an example in which a processor performs second analysis on a pathological slide image based on a user input, according to some embodiments.

FIG. 15 is a flowchart for describing an example in which a processor performs second analysis on a pathological slide image based on a user input, according to some embodiments.

In operation 1510, the user 30 reviews the analysis results.

In other words, the processor 110 outputs the analysis results through the display device such that the user 30 may review the analysis results. Here, the analysis results refer to the results of the first analysis performed on the pathological slide image by the first machine learning model. For example, the analysis results may include information about at least one tissue and cell recognized from the pathological slide image. An example in which the processor 110 analyzes the pathological slide image through the first machine learning model is as described above with reference to FIGS. 10 and 11.

In operation 1520, the processor 110 determines whether modification of the analysis results is required.

For example, the processor 110 may receive a user input from the user 30 and determine, based on the received user input, whether the analysis results need to be modified. Here, the modification is a concept including not only changing the existing analysis result, but also deleting the existing analysis result or adding content not included in the existing analysis result.

When it is determined that the analysis results need to be modified, operation 1540 is performed, and when it is determined that the analysis results do not need to be modified, operation 1530 is performed.

In operation 1540, the processor 110 determines whether the number of items to be modified is excessive.

For example, the processor 110 may receive a user input from the user 30 and determine, based on the user input, whether the number of items to be modified is excessive.

When it is determined that the number of items to be modified is excessive, operation 1570 is performed, and when it is determined that the number of items to be modified is not excessive, operation 1550 is performed.

In operation 1550, the processor 110 receives an user input regarding overall modification.

The user 30 updates all items to be modified from the existing analysis results, and the processor 110 receives a user input corresponding to the updating by the user 30.

For example, the user input may be to generate information about tissues or cells. For example, the user input may be to add tissues and/or cells not included in the existing analysis results. In addition, the user input may be to add coordinates (i.e., coordinates corresponding to positions of tissues or cells on the pathological slide image) or types of tissues or cells included in the existing analysis results.

As another example, the user input may be to modify information about tissues or cells. For example, the user input may be to modify the coordinates or types of cells included in the existing analysis results. Also, the user input may be to modify a region or type of tissues included in the existing analysis results.

As another example, the user input may be to delete information about tissues or cells. For example, the user input may be to delete cells included in the existing analysis results. In addition, the user input may be to delete a region of tissues included in the existing analysis results.

In operation 1560, the processor 110 applies the modification according to the user input.

Here, the modification is a concept including not only changing the existing analysis result, but also deleting the existing analysis result or adding content not included in the existing analysis result.

In operation 1530, the processor 110 generates second biomarker expression information.

When it is determined that there is no modification in the analysis results through operation 1520, the processor 110 may regard the first biomarker expression information as the second biomarker expression information. Alternatively, apart from the first biomarker expression information, the processor 110 may generate the second biomarker expression information based on the existing analysis results. In this case, the processor 110 may generate the second biomarker expression information by using the third machine learning model.

In a case in which operation 1530 is performed after operation 1560, the processor 110 generates the second biomarker expression information based on the content of the modification according to the user input. In this case, the processor 110 generates the second biomarker expression information based on the content of the modification according to the user input, by using the third machine learning model.

In operation 1570, the processor 110 receives a user input regarding partial modification.

Compared to operation 1550, the user input in operation 1570 may be to update only some of the items that need to be modified in the existing analysis results. An example of the content of the user input is as described above with reference to operation 1550.

In operation 1580, the processor 110 updates the first machine learning model.

The processor 110 may train the first machine learning model by using information modified through operation 1570, and the existing analysis results by the first machine learning model. The information modified through operation 1570 may serve as a hint in training the first machine learning model. Thus, the processor 110 may adjust parameters of the first machine learning model based on the information modified through operation 1570.

For example, the processor 110 may train the first machine learning model by combining a patch extracted from the information modified through operation 1570 (hereinafter, referred to as 'patch A'), with a patch extracted from the existing analysis results (hereinafter, referred to as 'patch B'). Here, patch A may be used as a correct answer when calculating a loss function.

On the other hand, because there is no correct answer in patch B, an unsupervised learning method may be used when calculating the loss function. For example, the loss function between patch B and a correct answer may be calculated by regarding the existing analysis results according to patch B as the correct answer of patch B. Alternatively, features may be obtained by inputting patch B to the first machine learning model, and the loss function may be calculated to restore patch B by passing the obtained feature through a separate decoder network. Alternatively, the loss function may be calculated such that the features obtained by inputting patch B to the first machine learning model, and features obtained by inputting, to the first machine learning model, patch B subjected to a geometric transformation (e.g., image rotation, etc.) and/or an optical transformation (e.g., blurring, etc.) are similar to each other.

Meanwhile, the processor 110 may configure a mini-batch by appropriately adjusting the ratio of the number of patches A to the number of patches B, such that the effects of patches A and patches B appropriately balance. Alternatively, the processor 110 may apply weights to loss function A (the loss function calculated for patch A) and loss function B (the loss function calculated for patch B) at an appropriate ratio.

Meanwhile, the processor 110 may update all parameters of the first machine learning model. However, in order to prevent overfitting, the processor 110 may maintain the parameters between the input layer and a particular middle layer of the first machine learning model, and update only the parameters of the other layers.

In operation 1590, the processor 110 performs second analysis.

In other words, the processor 110 may reanalyze the pathological slide image by using the second machine learning model (e.g., a model obtained by training the first machine learning model). When the second analysis is completed, the processor 110 returns to operation 1510 and outputs results of the second analysis. Accordingly, the user 30 may review the results of the second analysis.

Referring back to FIG. 13, in operation 1320, the processor 110 generates second biomarker expression information based on the second analysis.

As described above with reference to operation 1530, the processor 110 may generate the second biomarker expression information by using the third machine learning model. For example, a process of generating the first biomarker expression information and a process of generating the second biomarker expression information may be similar to each other. However, the process of generating the second biomarker expression information may be different from the process of generating the first biomarker expression information in terms of the following aspects.

First, the processor 110 generates the second biomarker expression information based on the results of the second analysis. Here, the results of the second analysis refer to results of analyzing the pathological slide image by the second machine learning model.

In addition, the processor 110 may reanalyze the entire region of the pathological slide image, or may reanalyze only one or more particular regions designated by the user 30.

Also, in addition to the numerical values described above with reference to operation 1220, the processor 110 may quantify biomarker expression by using a formula additionally input by the user 30. For example, in a case of an immunohistochemistry test, a method of quantifying biomarker expression may include, in addition to simply calculating the proportion (%) of positive cells, an Allred score or an H-score calculated considering both staining intensity and staining proportion.

Meanwhile, the method of quantifying biomarker expression may be selected by the user 30 or preset in the user terminal 100. In addition, the user 30 may directly input a desired formula (a quantification method). However, the test method is not limited to immunohistochemical staining, and the user 30 may input a relevant formula based on an inference result, for any type of pathological slide image.

Meanwhile, although not illustrated in FIG. 13, the processor 110 may output the second biomarker expression information. In other words, the processor 110 may control the display device to output the results of the second analysis and/or the second biomarker expression information.

For example, results of reanalysis of the pathological slide image (i.e., the results of the second analysis) and/or results of reanalysis of biomarker expression (i.e., the second biomarker expression information) may be output on the screen of the display device. In detail, the existing analysis results described above with reference to FIG. 15, and a UI for receiving a user input may be output on the screen of the display device. In addition, a UI required for the process described above with reference to operation 1320 (e.g., receiving, from the user 30, an input of one or more particular regions or an input of a formula for quantifying biomarker expression) may be output on the screen of the display device.

In addition, the results of the first analysis and the results of the second analysis may be output for comparison on the screen of the display device. When outputting a result of the comparison, the processor 110 may overlay and output the results of the first analysis and the results of the second analysis on the pathological slide image, respectively. Also, the processor 110 may output only a summary of items among the results of the second analysis that differ from the results of the first analysis. For example, the processor 110 may output history and statistical information of tissues/cells changed from the results of the first analysis, etc.

In addition, the first biomarker expression information and the biomarker expression information may be output for comparison on the screen of the display device. Also, the processor 110 may output only a summary of items among the second biomarker expression information that differ from the first biomarker expression information. For example, the processor 110 may output a biomarker score changed from the first biomarker expression information, etc.

Hereinafter, an example in which the processor 110 receives a user input and outputs the results of second analysis and/or the second biomarker expression information will be described with reference to FIGS. 16 to 20.

FIGS. 16 to 20 are diagrams illustrating examples in which a processor receives a user input and outputs results of second analysis and/or second biomarker expression information, according to some embodiments.

Figure 16:
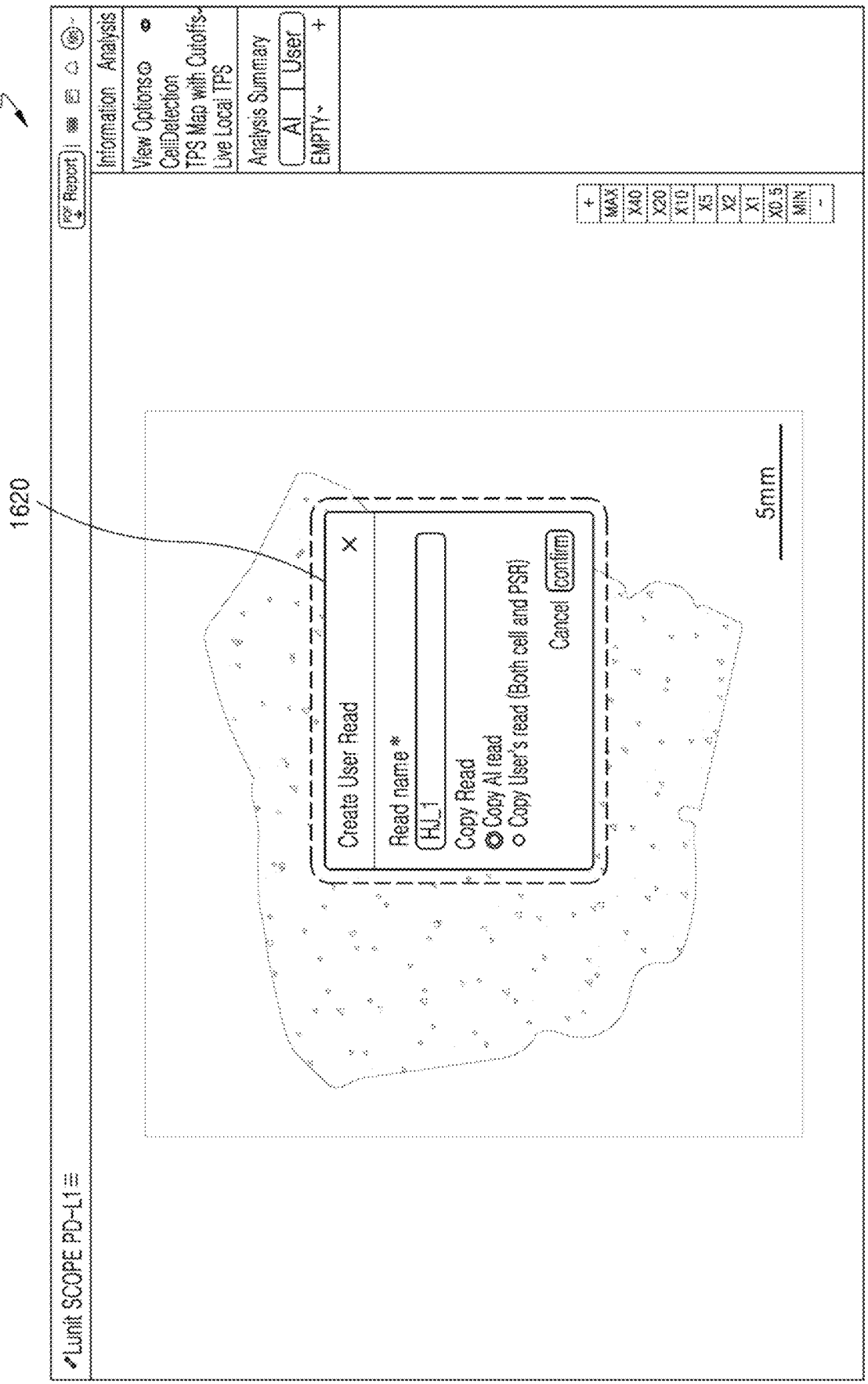
FIGS. 16 to 20 are diagrams illustrating examples in which a processor receives a user input and outputs results of second analysis and/or second biomarker expression information, according to some embodiments.

Referring to FIG. 16, the processor 110 may copy the results of the first analysis and store the results with a new name, in order to update the results of the first analysis based on the user input. The results of the second analysis based on the user input may be stored in the data stored with the new name.

For example, after the results of the first analysis are output on a screen 1610, a pop-up window 1620 for storing data with a new name may be displayed. The user 30 may input the name of a newly stored file through the pop-up window 1620. Alternatively, when the results of the first analysis are output on the screen 1610 and a user input for selecting a 'User' button in an 'Analysis Summary' panel of the screen 1610 is received, the processor 110 may switch to a user read mode and operate. In the user read mode, the processor 110 may receive a user input for drawing a region of interest (ROI) and/or a user input for editing cells to exclude a control tissue, and output the results of the second analysis based on the user input. For example, the results of the second analysis may include a TPS and/or a CPS calculated based on information updated based on a user input.

The user 30 may generate and edit his/her own user read data, but is not allowed to edit user read data generated by other users. Instead, the user is only allowed to read or copy user read data generated by other users. Accordingly, the user read data may be data generated by copying and modifying analysis results obtained by using the first machine learning model, or may be data generated by copying user read data generated by another user. The processor 110 may select, as representative data, one of pieces of user read data generated based on the pathological slide image, and include the representative data in an analysis report. Alternatively, in a case in which a user input for selecting user read data is not received, the processor 110 may select, as the representative data, AI read data that has not been modified according to a user input, or first generated user read data. In this case, the AI read data may include analysis results obtained by using the above-described first machine learning model.

In the user read mode, the processor 110 may calculate a TPS and a CPS only for a region selected by the user 30 drawing an ROI. The ROI may be drawn in the shape of a polygon, and an additional polygonal region may be drawn to exclude or additionally designate an object (or a region) within the drawn ROI.

In addition, tumor cells detected in the selected ROI may be modified through the following process. For example, the processor 110 may receive a user input for changing, to PD-L1-positive or -negative tumor cells, cells detected by the first machine learning model. As another example, the processor 110 may receive a user input for designating, as PD-L1-positive or -negative tumor cells, cells, the classes of which are not indexed. As another example, the processor 110 may receive a user input excluding cells that cannot be identified as positive or negative.

Figure 17:
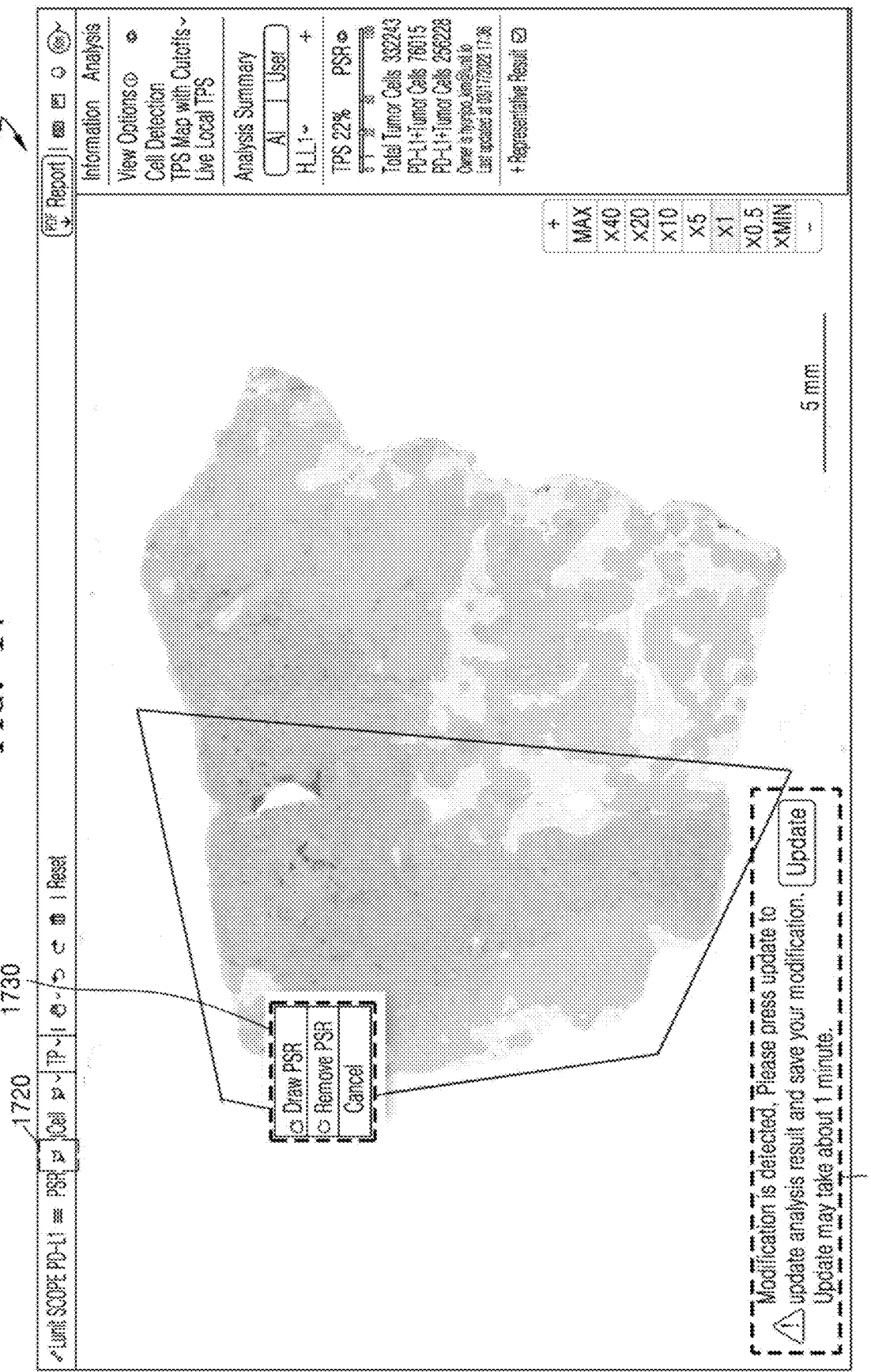

Referring to FIG. 17, the processor 110 may perform, based on a user input, modification to delete or newly draw a region to be reanalyzed in the pathological slide image. For example, the processor 110 may detect modification based on a user input through UIs 1720 and 1730 output on a screen 1710, and display, on the screen 1710, a pop-up window 1740 for asking whether to confirm the region to be reanalyzed. The processor 110 may reanalyze the pathological slide image based on a user input (i.e., a user input for determining the region to be reanalyzed) received through the pop-up window 1740.

Figure 18:
Figure 19:
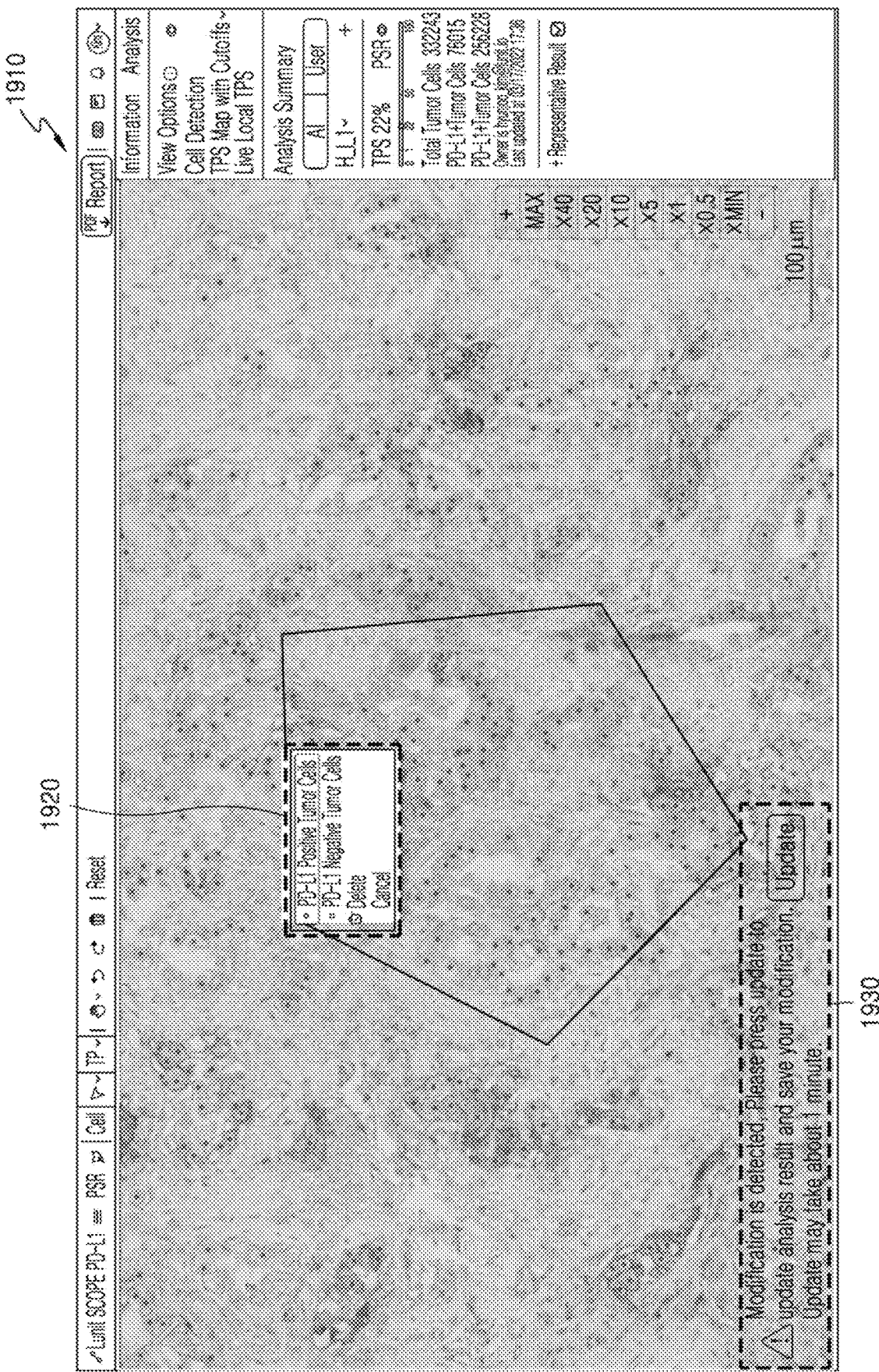
Figure 20:
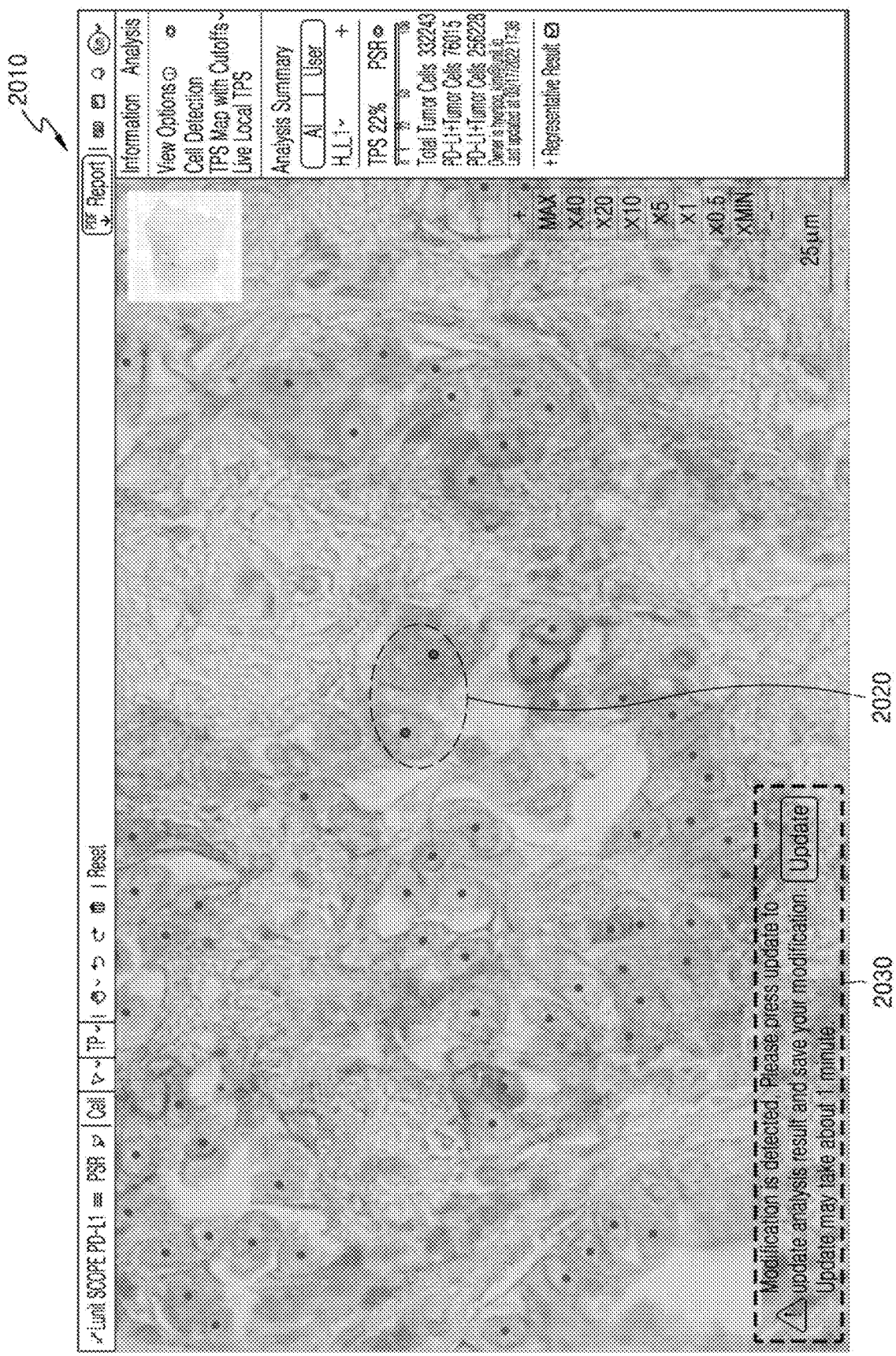

Referring to FIGS. 18 to 20, the processor 110 may update (e.g., add, modify, or delete), based on a user input, information about the types, positions, and/or presence or absence of previously analyzed tissues and/or cells. For example, the processor 110 may detect modification based on a user input through UIs 1820, 1920, and 2020 output on screens 1810, 1910, and 2010, and display pop-up windows 1830, 1930, and 2030 for asking whether to update results of previous analysis, on the screens 1810, 1910, and 2010, respectively. The processor 110 may reanalyze the pathological slide image, based on the user input (a user input for instructing to update the results of the previous analysis) received through the pop-up windows 1830, 1930, and 2030.

Referring back to FIG. 4, in operation 430, the processor 110 outputs a report including medical information about at least some regions included in the pathological slide image, based on at least one of the first biomarker expression information or the second biomarker expression information. For example, the processor 110 may generate the report and control the display device to output the generated report.

For example, the report may include at least one of medical information based on at least one selected from among the first analysis, the second analysis, the first biomarker expression information, or the second biomarker expression information, and medical information based on a result of comparing the first biomarker expression information with the second biomarker expression information.

In detail, the processor 110 may generate and provide a report including medical information about at least some regions included in the pathological slide image, based on results of analysis of the pathological slide including the first analysis and the second analysis, and results of biomarker analysis including the first biomarker expression information and the second biomarker expression information. For example, the report may be provided in the form of a file, data, text, an image, etc. that may be output through the user terminal 100 and/or the display device. Here, the medical information may refer to any information that may be extracted from a medical image and is medically meaningful. For example, the medical information may include an area, location, and size of a tumor cell in the medical image, diagnostic information regarding cancer, information associated with a subject's possibility of developing cancer, and/or a medical conclusion associated with cancer treatment. In addition, the medical information may include not only a quantified numerical value that may be obtained from a medical image, but also information obtained by visualizing the numerical value, predictive information according to the numerical value, image information, statistical information, and the like.

The user 30 may select one or more from among the first analysis, the second analysis, the first biomarker expression information, and the second biomarker expression information, and the processor 110 generates a report including medical information based on the selection by the user 30. In addition, a result of comparing the first analysis and the first biomarker expression information with the second analysis and the second biomarker expression information may be included in the report.

In addition, the processor 110 may output medical information about whether the subject responds to immuno-oncology therapy. For example, the processor 110 may generate and provide a report including results generated in a process of predicting whether the subject responds to immuno-oncology therapy.

In detail, the processor 110 may output at least one of a result of detecting one or more target items, an immunophenotype of at least some regions in the pathological slide image, information associated with the immunophenotype, a result of predicting responsiveness to immuno-oncology therapy, or the density of immune cells in at least some regions in the pathological slide image. As the processor 110 provides the user terminal 100 or the display device with the results generated in the process of predicting the responsiveness to immuno-oncology therapy, the user terminal 100 or the display device may output the received results.

For example, the processor 110 may output a target item detection result for at least some regions in the pathological slide image. For example, a pathological slide image including label information for each target item may be output. The pathological slide image may be output such that target items in region units are indicated with masks, and target items in cell units are indicated with center points of cell nuclei or bounding boxes.

As another example, the processor 110 may visualize and output an immunophenotypic feature map of the pathological slide image by using an expression method such as a mini map, a heat map, and/or a label map.

In another embodiment, the processor 110 may visualize and output, as a result of predicting the responsiveness to immuno-oncology therapy for at least some regions in the pathological slide image, a responsiveness score map (a respond/non-respond score map) by using an expression method such as a heat map and/or a label map, based on an immunophenotype, an activity score, a responsiveness score (a respond score and/or a non-respond score).

In another embodiment, the processor 110 may output the density of immune cells for each region for all and/or some regions of the pathological slide image. For example, the processor 110 may output a numerical value about the density of immune cells for each region for all and/or some regions of the pathological slide image, or may output a bar graph.

In another embodiment, the processor 110 may output the distribution of immunophenotypes of the subject expressed in a circle plot. For example, the processor 110 may output an analysis result including a bar graph representing the density of immune cells for each region, and a circle plot representing the distribution of immunophenotypes of the subject.

The processor 110 may receive, from an external system (e.g., an information processing system), results generated in a process of predicting whether the subject respond to immuno-oncology therapy, and output the received results. Accordingly, the user 30 may visually and intuitively recognize the results generated in the process of predicting whether the subject responds to immuno-oncology therapy.

Figure 21:
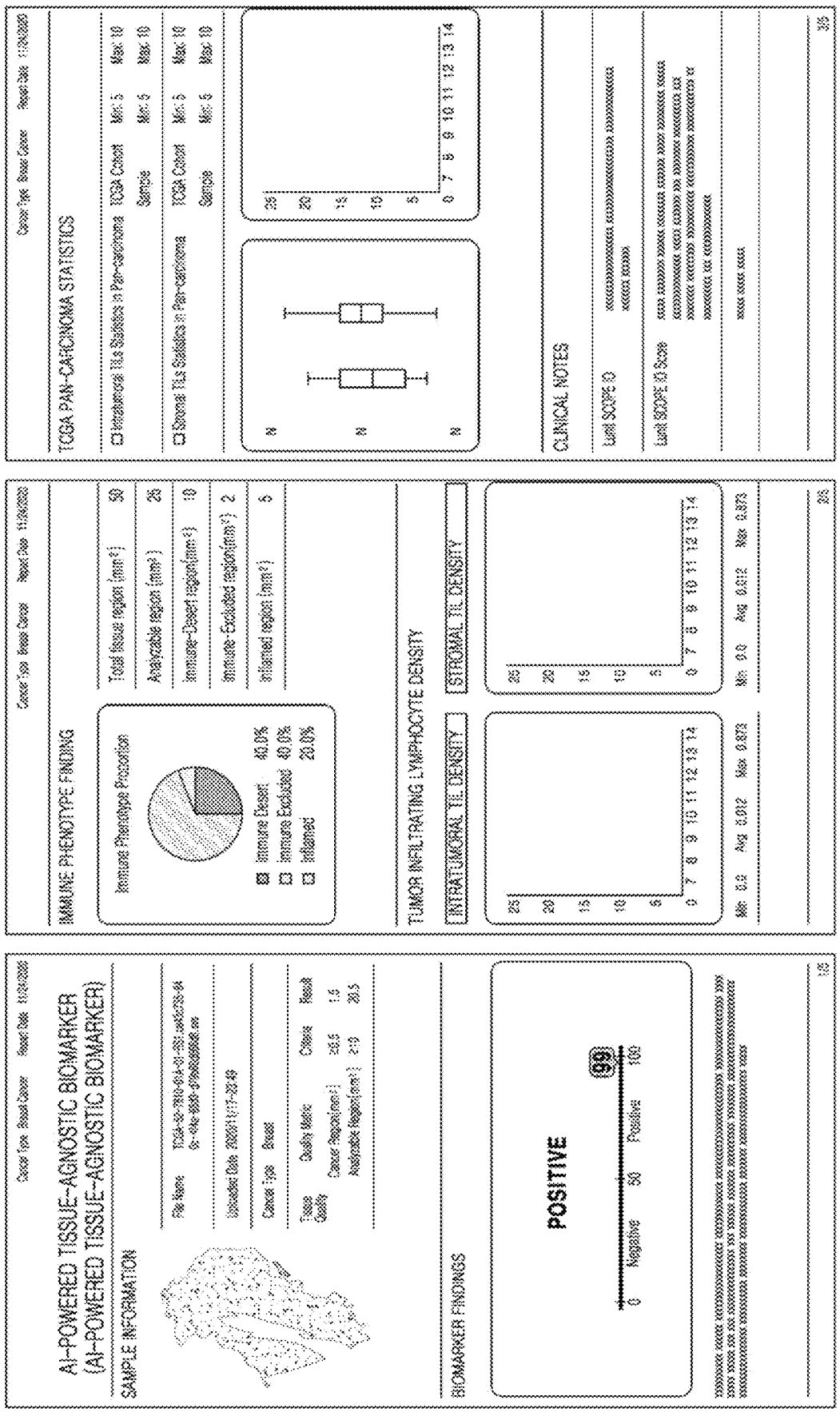
FIG. 21 is a diagram illustrating examples of reports according to some embodiments.

FIG. 21 is a diagram illustrating examples of reports according to some embodiments.

FIG. 21 illustrates reports in which various types of medical information are described in various forms. However, the form of the report is not limited to those illustrated in FIG. 21. In other words, as long as the user 30 may intuitively and accurately recognize medical information, the form of the report is not limited.

For example, the processor 110 may generate a report including a score representing a final prediction result on the subject (whether the subject is a responder or a non-responder) (e.g., a score between 0 and 1, indicating probability that the subject is a responder and/or a non-responder). Additionally or alternatively, the processor 110 may generate a report including information about a cut-off value for determining a responder or a non-responder. Additionally or alternatively, the processor 110 may generate a report including the distribution of immunophenotypes and/or TIL densities (e.g., a minimum, a maximum, an average, etc.) in the pathological slide image. For example, the processor 110 may generate a report including the distribution of TIL densities for each region of interest classified into three immunophenotypes, and a minimum, a maximum, and an average thereof. Additionally or alternatively, the processor 110 may generate a report including an immunophenotype map in which a region of interest in the pathological slide image is classified into three immunophenotypes.

By performing some embodiments of the disclosure on pathological images (e.g., pathological slide images, etc.) obtained before and/or after immunotherapy, the processor 110 may identify a mechanism of acquired resistance and provide customized treatment policies for each resistance mechanism. For example, the processor 110 may predict a treatment result for each of immuno-oncology therapy administered to the subject and/or other immuno-oncology therapies, by performing analysis by using input data such as a pathological image of the subject who has received treatment with immuno-oncology therapy and the type of a therapeutic agent administered to the subject. In some embodiments, the processor 110 may output information about at least one immuno-oncology therapy suitable for the subject, from among a plurality of immuno-oncology therapies, based on a result of predicting whether the subject responds to immuno-oncology therapy. For example, in a case in which the subject is determined as a responder, the processor 110 may generate a report including an immuno-oncology therapy product having a high response potential and/or a combination of such products.

In addition, the report may include a pathological slide image, information of the subject, basic information, and/or a result of prediction (whether the subject is a responder or a non-responder). In addition, the report may include a graph representing the proportion of immunophenotypes, numerical values, and information about TIL density (e.g., the distribution of densities, etc.). In addition, the report may include graphs representing statistical results (e.g., TCGA PANCARCINOMASTATISTICS) and/or analysis results, clinical notes, etc. In addition, the report may include information about references (e.g., academic references), etc. In addition, the report may include results generated in the prediction process (e.g., an immunophenotype map image, feature statistics, etc.) and/or information used in the prediction process.

Figure 22:
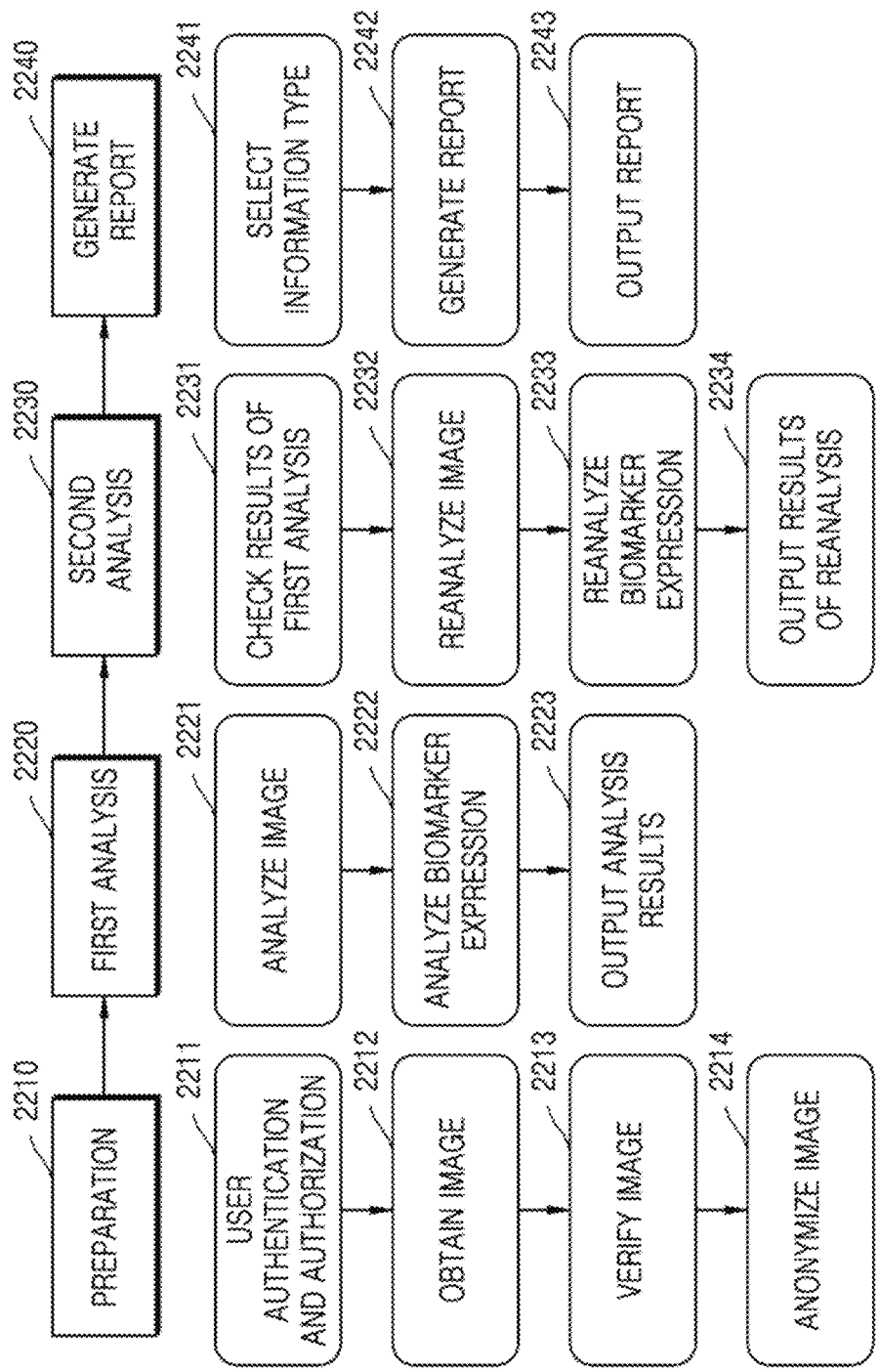
FIG. 22 is a flowchart for describing an example of a method of processing a pathological slide image according to some embodiments.

FIG. 22 is a flowchart for describing an example of a method of processing a pathological slide image according to some embodiments.

Referring to FIG. 22, the method of processing a pathological slide image includes operations that are processed, in a time-series manner, by the processor 110 described above with reference to FIGS. 1 to 21. Therefore, the descriptions of the processor 110 provided above with reference to FIGS. 1 to 22, which are even omitted below, may also be applied to the method of processing a pathological slide image of FIG. 22.

The processor 110 may process a pathological slide image by performing a preparation operation 2210, a first analysis operation 2220, a second analysis operation 2230 and a report generation operation 2240.

In the preparation operation 2210, the processor 110 performs user authentication and authorization 2211. As the processor 110 performs a user authentication and authorization process, the user 30 may log in to the user terminal 100.

Thereafter, the processor 110 obtains an image (2212). For example, the processor 110 may read the pathological slide image from the memory 120 in the user terminal 100, or may receive the pathological slide image from an external device connected to the user terminal 100. In a case in which the user terminal 100 receives the pathological slide image from the external device, the processor 110 may store the received image in the memory 120.

Thereafter, the processor 110 verifies the image (2213). For example, the processor 110 may perform at least one of first verification on a staining method corresponding to the pathological slide image, second verification on metadata corresponding to the pathological slide image, or third verification on an image pyramid corresponding to the pathological slide image.

Thereafter, the processor 110 performs anonymization on the image (2214). The processor 110 may perform the anonymization on the pathological slide image such that the subject cannot be specified (i.e., identified) from the pathological slide image. For example, the processor 110 may delete or mask all subject-identifiable information from the pathological slide image.

In the first analysis operation 2220, the processor 110 analyzes the image (2221). The processor 110 identifies information about at least one tissue and cell expressed in the pathological slide image. For example, the processor 110 may identify (first analysis) information about the tissue and cell from the pathological slide image by using the first machine learning model.

Thereafter, the processor 110 performs biomarker expression analysis (2222). The processor 110 generates first biomarker expression information based on the information identified through operation 2221. For example, according to an analysis guide of each biomarker, the processor 110 may automatically quantify the expression of the biomarker and analyze the expression rate of the biomarker. The processor 110 may generate the first biomarker expression information by using the third machine learning model. Here, the third machine learning model may be the same model as or a model different from the first machine learning model.

Thereafter, the processor 110 outputs analysis results (2223). For example, the processor 110 may output results of the first analysis and/or the first biomarker expression information. In other words, the processor 110 may control the display device to output the results of the first analysis and/or the first biomarker expression information.

In the second analysis operation 2230, the processor 110 checks the results of the first analysis (2231). The processor 110 outputs the results of the first analysis through the display device such that the user 30 may review the results of the first analysis. Here, the analysis results refer to the analysis results on the pathological slide image by the first machine learning model. For example, the analysis results may include information about at least one tissue and cell recognized from the pathological slide image.

Thereafter, the processor 110 reanalyzes the image (2232). For example, the processor 110 may receive a user input from the user 30 and reanalyze the pathological slide image based on the user input. Here, the reanalysis is a concept including not only changing the existing analysis result, but also deleting the existing analysis result or adding content not included in the existing analysis result. For example, the processor 110 may reanalyze (second analysis) information about tissues and cells from the pathological slide image by using the second machine learning model (e.g., a model obtained by training the first machine learning model).

Thereafter, the processor 110 performs biomarker expression reanalysis (2233). The processor 110 generates second biomarker expression information based on the second analysis. For example, the processor 110 may generate the second biomarker expression information by using the third machine learning model. A process of generating the first biomarker expression information and a process of generating the second biomarker expression information may be similar to each other.

Thereafter, the processor 110 outputs results of the reanalysis (2223). For example, the results of the reanalysis of the pathological slide image (i.e., the results of the second analysis) and/or results of reanalysis of biomarker expression (i.e., the second biomarker expression information) may be output on the screen of the display device.

In the report generation operation 2240, the processor 110 selects, based on a user input or a preset item, a type of medical information (2241), generates a report according to the selected type (2242), and outputs the generated report (2243).

As described above, as reanalysis based on update by the user 30 is performed on analysis results on the pathological slide image obtained by a machine learning model, the accuracy of reading the pathological slide image may be improved.

Meanwhile, the above-described method may be written as a computer-executable program, and may be implemented in a general-purpose digital computer that executes the program by using a computer-readable recording medium. In addition, the structure of the data used in the above-described method may be recorded in a computer-readable recording medium through various units. The computer-readable recording medium includes a storage medium, such as a magnetic storage medium (e.g., ROM, RAM, a universal serial bus (USB) drive, a floppy disk, a hard disk, etc.) and an optically readable medium (e.g., a CD-ROM, a DVD, etc.).

It will be understood by those of skill in the art that the disclosure may be implemented in a modified form without departing from the intrinsic characteristics of the descriptions provided above. Therefore, the disclosed methods should be considered in an illustrative rather than a restrictive sense, and the scope of the disclosure should be defined by claims rather than the foregoing description, and should be construed to include all differences within the scope equivalent thereto.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A computing device comprising:
at least one memory; and
at least one processor configured to:
perform first analysis on a pathological slide image, by using a first machine learning model, to identify cell information about at least one cell expressed in the pathological slide image,
generate first biomarker expression information about the pathological slide image based on the cell information identified by the first machine learning model,
receive a user input for updating the cell information,
perform second analysis on the pathological slide image based on the user input to update the cell information,
generate second biomarker expression information about the pathological slide image based on the updated cell information, and
control a display device to output a report including medical information about at least some regions included in the pathological slide image, based on the second biomarker expression information,
wherein the user input is at least one of an input to add information about a staining expression level of the cell, an input to modify information about the staining expression level of the cell, or an input to delete information about the staining expression level of the cell.

2. The computing device of claim 1, wherein
the second analysis is performed by a second machine learning model that is a machine learning model corresponding to the first machine learning model or a machine learning model obtained by updating the first machine learning model.

3. The computing device of claim 2, wherein the second machine learning model is obtained by training the first machine learning model based on information obtained by modifying results of the first analysis according to the user input.

4. The computing device of claim 1, wherein the first biomarker expression information and the second biomarker expression information are generated by a third machine learning model.

5. The computing device of claim 1, wherein the user input comprises an input for updating results of the first analysis after a user confirms the results of the first analysis according to priorities that are set based on the first biomarker expression information.

6. The computing device of claim 1, wherein the report comprises at least one of first medical information or second medical information,
wherein the first medical information is based on at least one of results of the first analysis, results of the second analysis, the first biomarker expression information, or the second biomarker expression information, and
wherein the second medical information is based on a result of comparing the first biomarker expression information with the second biomarker expression information.

7. The computing device of claim 1, wherein the processor is further configured to, before performing the first analysis on the pathological slide image, verify the pathological slide image and perform anonymization on subject-identifiable information among information corresponding to the pathological slide image.

8. The computing device of claim 7, wherein the processor is further configured to perform at least one of first verification on a staining method corresponding to the pathological slide image, second verification on metadata corresponding to the pathological slide image, or third verification on an image pyramid corresponding to the pathological slide image.

9. The computing device of claim 1, wherein the processor is further configured to control the display device to output results of the first analysis and the first biomarker expression information.

10. The computing device of claim 1, wherein the processor is further configured to control the display device to output the second biomarker expression information.

11. A method of processing a pathological slide image, the method comprising:
performing first analysis on a pathological slide image, by using a first machine learning model, to identify cell information about at least one cell expressed in the pathological slide image;
generating first biomarker expression information about the pathological slide image based on the cell information identified by the first machine learning model;
receiving a user input for updating the cell information;
performing second analysis on the pathological slide image based on the user input to update the cell information;
generating second biomarker expression information about the pathological slide image based on the updated cell information; and
outputting a report including medical information about at least some regions included in the pathological slide image, based on the second biomarker expression information,
wherein the user input is at least one of an input to add information about a staining expression level of the cell, an input to modify information about the staining expression level of the cell, or an input to delete information about the staining expression level of the cell.

12. The method of claim 11, wherein
the second analysis is performed by a second machine learning model that is a machine learning model corresponding to the first machine learning model or a machine learning model obtained by updating the first machine learning model.

13. The method of claim 12, wherein the second machine learning model is obtained by training the first machine learning model based on information obtained by modifying, according to the user input, results of the first analysis.

14. The method of claim 11, wherein the first biomarker expression information and the second biomarker expression information are generated by a machine learning model.

15. The method of claim 11, wherein the user input comprises an input for updating at least some of results of the first analysis after a user confirms the results of the first analysis according to priorities that are set based on the first biomarker expression information.

16. A non-transitory computer-readable recording medium having recorded thereon a program for causing a computer to execute the method of claim 11.

* * * * *